US012797588B2

(12) United States Patent
Okamoto et al.

(10) Patent No.: US 12,797,588 B2
(45) Date of Patent: Nov. 17, 2026

(54) BALLOON CATHETER

(71) Applicant: GOODMAN CO., LTD., Nagoya (JP)

(72) Inventors: Mitsumasa Okamoto, Seto (JP); Shuhei Yamamoto, Seto (JP); Shizuya Yoshinaga, Seto (JP); Shoma Kondo, Seto (JP); Yuta Nakamura, Seto (JP)

(73) Assignee: GOODMAN CO., LTD., Nagoya (JP)

( * ) Notice: Subject to any disclaimer, the term of this patent is extended or adjusted under 35 U.S.C. 154(b) by 393 days.

(21) Appl. No.: 18/441,720

(22) Filed: Feb. 14, 2024

(65) Prior Publication Data

US 2024/0181226 A1 Jun. 6, 2024

Related U.S. Application Data

(63) Continuation of application No. PCT/JP2022/028567, filed on Jul. 25, 2022.

(30) Foreign Application Priority Data

Aug. 31, 2021 (JP) ................................ 2021-140754

(51) Int. Cl.
*A61B 17/22* (2006.01)
*A61M 25/10* (2013.01)

(52) U.S. Cl.
CPC ......... *A61M 25/1002* (2013.01); *A61B 17/22* (2013.01); *A61B 2017/22001* (2013.01)

(58) Field of Classification Search
CPC ...... A61M 2025/1086; A61M 25/1002; A61M 2025/109; A61M 25/10; A61M 25/104; A61M 25/1006; A61B 17/22; A61B 2017/22001; A61B 2017/22051
See application file for complete search history.

(56) References Cited

U.S. PATENT DOCUMENTS 5,324,260 A 6/1994 O'Neill et al.
6,027,510 A 2/2000 Alt
8,066,726 B2 * 11/2011 Kelley ........... A61B 17/320725 606/159

(Continued)

FOREIGN PATENT DOCUMENTS

CN 107921246 A 4/2018
CN 109363808 A 2/2019

(Continued)

OTHER PUBLICATIONS

Oct. 14, 2025—(IN) Examination Report—App 202417015292.

(Continued)

*Primary Examiner* — Katherine M Shi

(74) *Attorney, Agent, or Firm* — Banner & Witcoff, Ltd.

(57) ABSTRACT

A balloon catheter includes a catheter shaft, a balloon, and a protruding portion. The balloon is connected to the catheter shaft. The balloon includes an inflatable portion and a distal end connecting portion. The protruding portion protrudes radially outward with respect to a center axis of the catheter shaft. The protruding portion has at least one of a first protruding portion provided on the distal end connecting portion of the balloon, or a second protruding portion provided on a distal end extending portion. The distal end connecting portion includes at least a region where a protrusion amount is smaller than a protrusion amount of the protruding portion.

11 Claims, 33 Drawing Sheets

(56) References Cited

U.S. PATENT DOCUMENTS

| | | | | |
|---|---|---|---|---|
| 9,402,983 | B1 * | 8/2016 | Nath | A61M 25/1002 |
| 10,632,291 | B2 | 4/2020 | Shimada | |
| 10,842,971 | B2 | 11/2020 | Iwano et al. | |
| 11,679,242 | B2 | 6/2023 | Okamoto et al. | |
| 2004/0013869 | A1 | 1/2004 | Draveling | |
| 2004/0225318 | A1 | 11/2004 | Eidenschink et al. | |
| 2005/0203563 | A9 * | 9/2005 | Pederson | A61F 2/958 606/192 |
| 2006/0182873 | A1 | 8/2006 | Klisch et al. | |
| 2008/0132836 | A1 | 6/2008 | Burton et al. | |
| 2013/0053768 | A1 | 2/2013 | Hennessey | |
| 2013/0131594 | A1 | 5/2013 | Bonnette et al. | |
| 2014/0324079 | A1 * | 10/2014 | Silvestro | A61B 17/32075 606/159 |
| 2017/0197065 | A1 | 7/2017 | Shimada | |
| 2018/0043140 | A1 | 2/2018 | Iwano et al. | |
| 2018/0177985 | A1 | 6/2018 | Nakagawa et al. | |
| 2018/0214289 | A1 | 8/2018 | Yang et al. | |
| 2020/0078197 | A1 | 3/2020 | Yang et al. | |
| 2021/0113820 | A1 | 4/2021 | Okamoto et al. | |
| 2021/0113821 | A1 | 4/2021 | Okamoto et al. | |
| 2023/0398335 | A1 | 12/2023 | Kojima et al. | |

FOREIGN PATENT DOCUMENTS

| | | | | |
|---|---|---|---|---|
| CN | 110430842 | A | 11/2019 | |
| CN | 111194187 | A * | 5/2020 | A61M 25/1006 |
| CN | 210963508 | U | 7/2020 | |
| CN | 112203712 | A | 1/2021 | |
| EP | 3281669 | A1 | 2/2018 | |
| EP | 3795200 | A1 | 3/2021 | |
| JP | 2017-123928 | A | 7/2017 | |
| JP | 2020-000677 | A | 1/2020 | |
| JP | 2020-110419 | A | 7/2020 | |
| WO | 2020-012850 | A1 | 1/2020 | |
| WO | 2020-012851 | A1 | 1/2020 | |
| WO | 2022-102766 | A1 | 5/2022 | |

OTHER PUBLICATIONS

Dec. 16, 2025—(KR) Request for the Submission of an Opinion—App 10-2024-7005686.

Sep. 27, 2022—International Search Report—Intl App PCT/JP2022/028567.

Aug. 8, 2025—(CA) Office Action—App 3228244.

Jul. 10, 2025—(EP) Extended EP Search Report—App 22864110.6.

Jun. 25, 2025—(AU) Second Examination Report—AU App. 2022338382.

Mar. 5, 2024—(WO) International Preliminary Report on Patentability—PCTJP2022028567, Eng Tran.

Jul. 16, 2024—(JP) Office Action—App 2023-545159, Eng Tran.

Nov. 13, 2025—(CN) First Office Action—App 202280021617.4, Eng Tran.

* cited by examiner

BALLOON CATHETER

REFERENCE TO RELATED APPLICATIONS

This application is a Continuation application of International Application No. PCT/JP2022/028567, filed Jul. 25, 2022, which claims priority from Japanese Patent Application No. 2021-140754, filed on Aug. 31, 2021. This disclosure of the foregoing application is hereby incorporated by reference in its entirety.

BACKGROUND ART

A balloon catheter in which linear protruding portions are provided on a balloon is known. A linear protruding portion is provided over the entire region of a balloon in the axial direction, over a proximal end side cone region, a straight tube region, and a distal end side cone region of the balloon. The linear protruding portions protrude outward from the outer surface of the balloon.

SUMMARY

There is a problem in which, when a balloon is inserted into a blood vessel, a linear protruding portion provided in a distal end side cone region may catch on the interior wall or the like of the blood vessel, thereby reducing passability of the balloon.

The present disclosure aims to provide a balloon catheter that makes it possible to achieve excellent passability of a balloon even when a protruding portion is provided on the distal end portion of the balloon.

A balloon catheter according to the present disclosure includes a catheter shaft, a balloon, and a protruding portion. The catheter shaft extends in an extending direction between a first proximal end portion and a first distal end portion. The balloon is connected to the catheter shaft at a position where the distance to the first distal end portion is shorter than the distance to the first proximal end portion. The balloon includes an inflatable portion and a distal end connecting portion. The inflatable portion has a cylindrical shape extending in the extending direction. The distal end connecting portion is a portion extending to a side opposite the inflatable portion from a second distal end portion of the inflatable portion. The second distal end portion is one end portion of the inflatable portion that is closer to the first distal end portion of the catheter shaft than the other end portion of the inflatable portion in the extending direction. A diameter of the end portion of the distal end connecting portion that is connected to the inflatable portion is larger than a diameter of a third distal end portion of the distal end connecting portion which is an end portion on a side opposite the end portion connected to the inflatable portion. The distal end connecting portion connects to the catheter shaft at the third distal end portion. The protruding portion protrudes radially outward with respect to a center axis of the catheter shaft. The protruding portion has at least one of a first protruding portion provided on the distal end connecting portion of the balloon, or a second protruding portion provided on a distal end extending portion which is a portion between the third distal end portion of the balloon and the first distal end portion of the catheter shaft in the extending direction. The distal end connecting portion includes at least a region where a protrusion amount is smaller than a protrusion amount of the protruding portion, between the second distal end portion and an end portion of the protruding portion nearest to the second distal end portion.

With the balloon catheter, the size of the region where the protruding portion is provided on the distal end connecting portion can be smaller than it can be when the protruding portion is provided over the entire region of the distal end connecting portion. Therefore, the balloon catheter makes it possible to achieve excellent passability of the balloon inside the blood vessel even when the protruding portion is provided.

BRIEF DESCRIPTION OF DRAWINGS

Embodiments will be described below in detail with reference to the accompanying drawings in which.

DESCRIPTION

Figure 1:
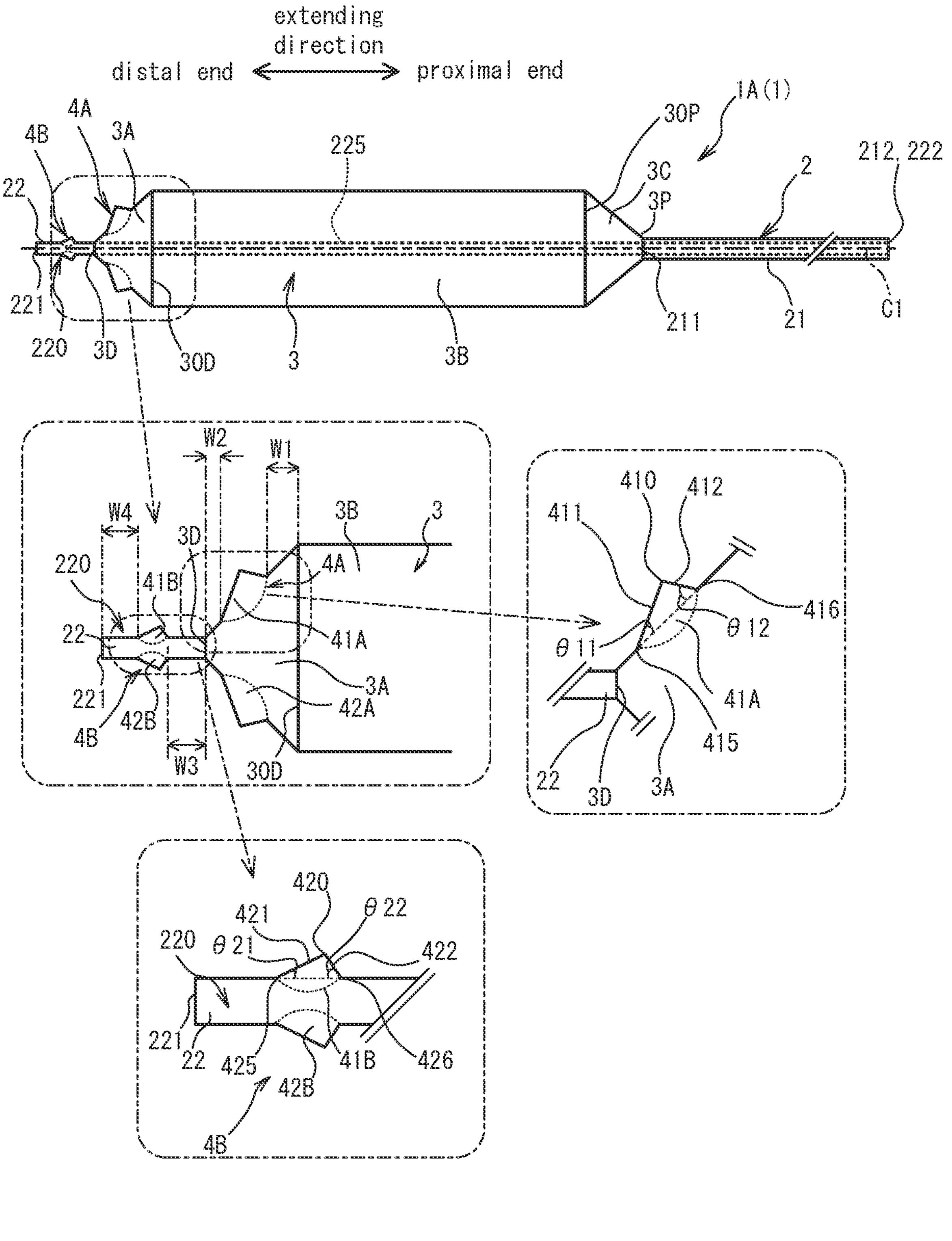
FIG. 1 is a view of a balloon catheter from the side.

Embodiments (balloon catheters 1A to 1H) of a balloon catheter 1 according to the present disclosure will now be described with reference to the drawings. The referenced drawings are used to describe technical features that can be employed in the present disclosure. The described configuration and the like of the device is not intended to be limited thereto and is merely an example for explanation purposes. The balloon catheter 1 can dilate a stenotic lesion formed in a blood vessel by a balloon 3, or apply protruding portions 4 (protruding portions 4A to 4E, 4G, and 4I), to be described later, to a blood vessel.

First Embodiment (Balloon Catheter 1A)

The balloon catheter 1A will now be described with reference to FIG. 1 to FIG. 2. The balloon catheter 1A has a catheter shaft 2, the balloon 3, and protruding portions 4A and 4B.

Catheter Shaft 2

The catheter shaft 2 has a tubular shape. The balloon 3 is connected near an end portion on one side of the catheter shaft 2. A hub, not shown in the drawings, is connected to an end portion on the other side of the catheter shaft 2. The hub can supply compressed fluid to the balloon 3 via the catheter shaft 2.

The one side from among both ends of the catheter shaft 2 will be referred to as a distal end side. The other side from among both ends of the catheter shaft 2 will be referred to as a proximal end side. The direction extending along the catheter shaft 2 will be referred to as an extending direction. An axis passing through the center of the catheter shaft 2 and extending in the extending direction will be referred to as a center axis C1. In a cross-section cut on a plane perpendicular to the center axis C1 (hereinafter, simply referred to as a cross-section), the side near the center axis C1 in a radial direction centered on the center axis C1 will be referred to as the an inner side, and the side away from the center axis C1 will be referred to as an outer side.

The catheter shaft 2 has an outer tube 21 and an inner tube 22. The outer tube 21 and the inner tube 22 are both flexible. The inside diameter of the outer tube 21 is larger than the outside diameter of the inner tube 22. Other than a predetermined portion on the distal end side, the inner tube 22 is disposed inside the lumen of the outer tube 21. The predetermined portion on the distal end side of the inner tube 22 protrudes toward the distal end side from an end (hereinafter referred to as a distal end portion 211) on the distal end side of the outer tube 21. The end (hereinafter referred to as a distal end portion 221) on the distal end side of the inner tube 22 is disposed farther toward the distal end side than the distal end portion 211 of the outer tube 21. Hereinafter, the predetermined portion on the distal end side of the inner tube 22 will be referred to as a protruding portion 225. The end on the proximal end side of the outer tube 21 will be referred to as a proximal end portion 212. The end on the proximal end side of the inner tube 22 will be referred to as a proximal end portion 222. The hub is connected to at least the proximal end portion 212 of the outer tube 21. The material of the outer tube 21 and the inner tube 22 is not particularly limited; a polyamide resin may be used as an example.

The compressed fluid supplied from the hub flows through a space of the lumen of the outer tube 21 other than the lumen of the inner tube 22. A guide wire that is not shown in the drawings is inserted through the lumen of the inner tube 22.

Balloon 3

The balloon 3 can change shape between a deflated state and an inflated state, as a result of a change in internal pressure according to whether the compressed fluid is supplied from the hub not shown in the drawings. FIG. 1 shows the balloon 3 in the inflated state.

An end (hereinafter referred to as a distal end portion 3D) on the distal end side of the balloon 3 is connected by thermal welding to a portion farther toward the proximal end side than the distal end portion 221 of the protruding portion 225 of the inner tube 22. Hereinafter, the portion of the protruding portion 225 of the inner tube 22 that is between the portion where the distal end portion 3D of the balloon 3 is connected and the distal end portion 221 will be referred to as a distal end extending portion 220. Also, the end portion (hereinafter, referred to as a proximal end portion 3P) on the proximal end side of the balloon 3 is connected by thermal welding to near the distal end portion 211 of the outer tube 21. The distance between the distal end portion 3D of the balloon 3 and the distal end portion 221 of the inner tube 22 is shorter than the distance between the proximal end portion 3P of the balloon 3 and the proximal end portion 222 of the inner tube 22. The balloon 3 covers the protruding portion 225 of the inner tube 22 from the outside. The material of the balloon 3 is not particularly limited; a polyamide resin may be used as an example.

A distal end connecting portion 3A, an inflatable portion 3B, and a proximal end connecting portion 3C are defined in the balloon 3. The distal end connecting portion 3A is a region extending from the distal end portion 3D toward the proximal end portion 3P of the balloon 3 in the inflated state while increasing in diameter. The proximal end connecting portion 3C is a region extending from the proximal end portion 3P toward the distal end portion 3D of the balloon 3 in the inflated state while increasing in diameter. The inflatable portion 3B is a region sandwiched between the distal end connecting portion 3A and the proximal end connecting portion 3C of the balloon 3 in the inflated state, which has substantially the same diameter in the extending direction. The inflatable portion 3B has a tubular shape that extends in the extending direction in the inflated state. The side nearer to the distal end portion 221 of the inner tube 22 of the catheter shaft 2, i.e., the end portion on the distal end side, of the inflatable portion 3B will be referred to as a distal end portion 30D. The side nearer to the proximal end portion 222 of the inner tube 22 of the catheter shaft 2, i.e., the end portion on the proximal end side, of the inflatable portion 3B will be referred to as a proximal end portion 30P.

The distal end connecting portion 3A extends to the distal end side from the end portion that connects with the distal end portion 30D of the inflatable portion 3B toward the distal end portion 3D. The diameter of a cross-section of the distal end connecting portion 3A is largest at the end portion that is connected to the distal end portion 30D of the inflatable portion 3B, and smallest at the distal end portion 3D. The proximal end connecting portion 3C extends to the proximal end side from the end portion that is connected to the proximal end portion 30P of the inflatable portion 3B toward the proximal end portion 3P. The diameter of a cross-section of the proximal end connecting portion 3C is largest at the end portion that is connected to the proximal end portion 30P of the inflatable portion 3B, and smallest at the proximal end portion 3P.

Protruding Portion 4A

The protruding portion 4A is provided on the outer surface of the distal end connecting portion 3A of the balloon 3 and protrudes outward. The protruding portion 4A has protrusions 41A and 42A. The protrusions 41A and 42A face one another across the center axis C1. The protrusions 41A and 42A each have a conical shape. Of the protrusions 41A and 42A, an apex 410 of each protrusion 41A and 42A protrudes farthest outward. The bottom portions of the protrusions 41A and 42A are connected to the outer surface of the distal end connecting portion 3A of the balloon 3. The protrusions 41A and 42A have the same shape. The shortest distance between the bottom surfaces of the protrusions 41A and 42A and the apex 410 corresponds to the protrusion amount of the protruding portion 4A. Hereinafter, the shape of the protruding portion 4A will be described using the protrusion 41A as an example.

The portion of the bottom portion of the protrusion 41A that is nearest to the distal end portion 3D of the distal end connecting portion 3A will be referred to as a distal end portion 415. The portion of the side surface of the protrusion 41A that corresponds to a generating line that connects the apex 410 to the distal end portion 415 will be referred to as a distal end inclined portion 411. The distal end inclined portion 411 extends along the side surface of the protrusion 41A from the distal end portion 415 toward the apex 410. The portion of the bottom portion of the protrusion 41A that is nearest to the distal end portion 30D of the inflatable portion 3B will be referred to as a proximal end portion 416. The portion of the side surface of the protrusion 41A that corresponds to a generating line that connects the apex 410 to the proximal end portion 416 will be referred to as a proximal end inclined portion 412. The proximal end inclined portion 412 extends along the side surface of the protrusion 41A from the proximal end portion 416 toward the apex 410. In this case, the angle θ12 of the proximal end inclined portion 412 with respect to the distal end connecting portion 3A is greater than the angle θ11 of the distal end inclined portion 411 with respect to the distal end connecting portion 3A (i.e., θ11<θ12).

The proximal end portions 416 of the protrusions 41A and 42A are spaced apart from the distal end portion 30D of the inflatable portion 3B of the balloon 3 toward the distal end side. Therefore, the distal end connecting portion 3A of the balloon 3 includes a region W1 where the protruding portion 4A is not provided, between the proximal end portion 416 of the protruding portion 4A and the portion where the distal end portion 30D of the inflatable portion 3B connects in the extending direction. The distal end portion 415 of each of the protrusions 41A and 42A is spaced apart from the distal end portion 3D of the distal end connecting portion 3A of the balloon 3 toward the proximal end side. Therefore, the distal end connecting portion 3A of the balloon 3 includes a region W2 where the protruding portion 4A is not provided, between the distal end portion 415 of the protruding portion 4A and the distal end portion 3D in the extending direction.

Protruding Portion 4B

The protruding portion 4B is provided on the outer surface of the distal end extending portion 220 of the inner tube 22 and protrudes outward. The protruding portion 4B has protrusions 41B and 42B. The protrusions 41B and 42B face one another across the center axis C1. The protrusions 41B and 42B each have a conical shape. An apex 420 of each protrusion 41B and 42B protrudes farthest outward of the protrusions 41B and 42B. The bottom portions of the protrusions 41B and 42B are connected to the outer surface of the distal end extending portion 220. The protrusions 41B and 42B have the same shape. The protrusion amount of the protruding portion 4B is smaller than the protrusion amount of the protruding portion 4A. Hereinafter, the shape of the protruding portion 4B will be described using the protrusion 41B as an example.

The portion of the bottom portion of the protrusion 41B that is nearest to the distal end portion 221 of the inner tube 22 will be referred to as a distal end portion 425. The portion of the side surface of the protrusion 41B that corresponds to a generating line that connects the apex 420 to the distal end portion 425 will be referred to as a distal end inclined portion 421. The distal end inclined portion 421 extends along the side surface of the protrusion 41B from the distal end portion 425 toward the apex 420. The portion of the bottom portion of the protrusion 41B that is nearest to the distal end portion 3D of the distal end connecting portion 3A of the balloon 3 will be referred to as a proximal end portion 426. The portion of the side surface of the protrusion 41B that corresponds to a generating line that connects the apex 420 to the proximal end portion 426 will be referred to as a proximal end inclined portion 422. The proximal end inclined portion 422 extends along the side surface of the protrusion 41B from the proximal end portion 426 toward the apex 420. In this case, the angle θ22 of the proximal end inclined portion 422 with respect to the distal end extending portion 220 is greater than the angle θ21 of the distal end inclined portion 421 with respect to the distal end extending portion 220 (i.e., θ21<θ22).

The proximal end portions 426 of the protrusions 41B and 42B are spaced apart from the distal end portion 3D of the distal end connecting portion 3A of the balloon 3 toward the distal end side. Therefore, the distal end extending portion 220 of the inner tube 22 includes a region W3 where the protruding portion 4B is not provided, between the proximal end portion 426 of the protruding portion 4B and the portion where the distal end portion 3D of the distal end connecting portion 3A of the balloon 3 connects in the extending direction. The distal end portion 425 of each of the protrusions 41B and 42B is spaced apart from the distal end portion 221 of the inner tube 22 toward the proximal end side. Therefore, the distal end extending portion 220 of the inner tube 22 includes a region W4 where the protruding portion 4B is not provided, between the distal end portion 425 of the protruding portion 4B and the distal end portion 221 in the extending direction.

Example of Use

An example of use of the balloon catheter 1A will now be described. A case in which the balloon catheter 1A is used to dilate a stenotic lesion 90A that has occurred at a portion of the interior wall of a blood vessel 9 will be illustrated. The lumen of the stenotic lesion 90A is extremely small, and the diameter of the lumen is smaller than the diameter of the balloon 3 in the deflated state.

Figure 3A:
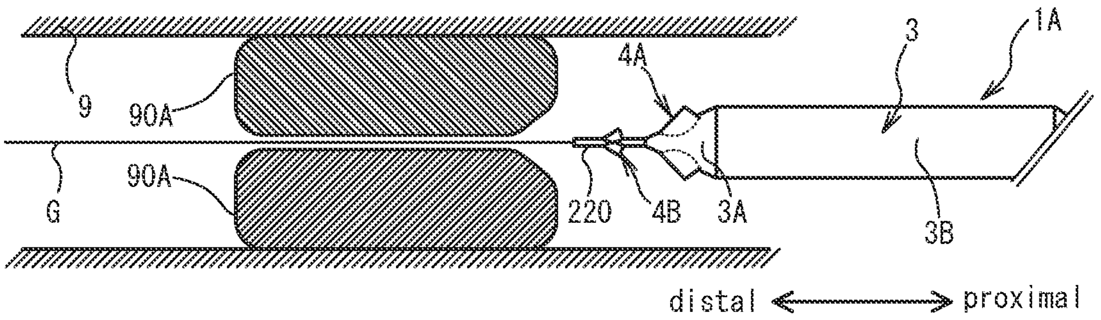
FIG. 3A is a view illustrating a usage example of the balloon catheter.

A guide wire G is inserted through the blood vessel 9. The balloon catheter 1A is prepared with the balloon 3 in the deflated state. As shown in FIG. 3A, a portion of the balloon catheter 1A that includes at least the balloon 3 is placed within the blood vessel 9. The guide wire G is inserted through the inner tube 22 of the balloon catheter 1A.

Figure 3B:
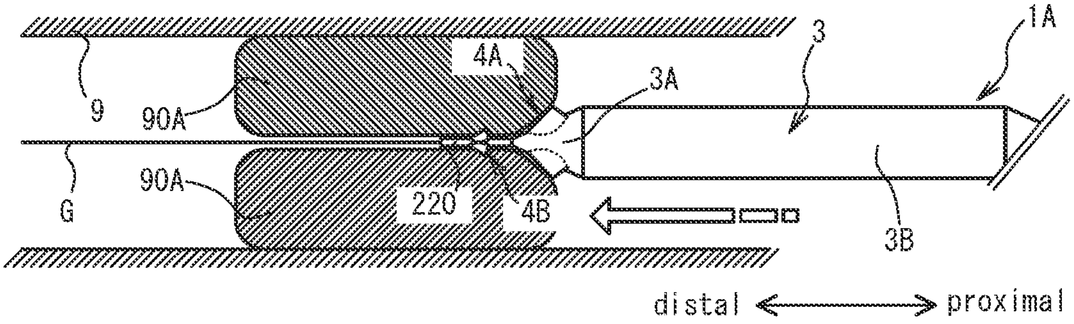
FIG. 3B is a view illustrating a usage example of the balloon catheter.

Next, the balloon catheter 1A is pushed into the blood vessel 9 along the guide wire G by operating the proximal end of the balloon catheter 1A. The balloon catheter 1A moves distally inside the blood vessel 9 toward the stenotic lesion 90A with the balloon 3 placed at the front in the moving direction. The distal end connecting portion 3A of the balloon 3 reaches the area near the proximal end portion of the stenotic lesion 90A. As shown in FIG. 3B, only a portion on the distal end side of the distal end connecting portion 3A enters the proximal end portion of the lumen of the stenotic lesion 90A. Then, movement of the balloon catheter 1A toward the distal side is stopped.

Figure 3C:
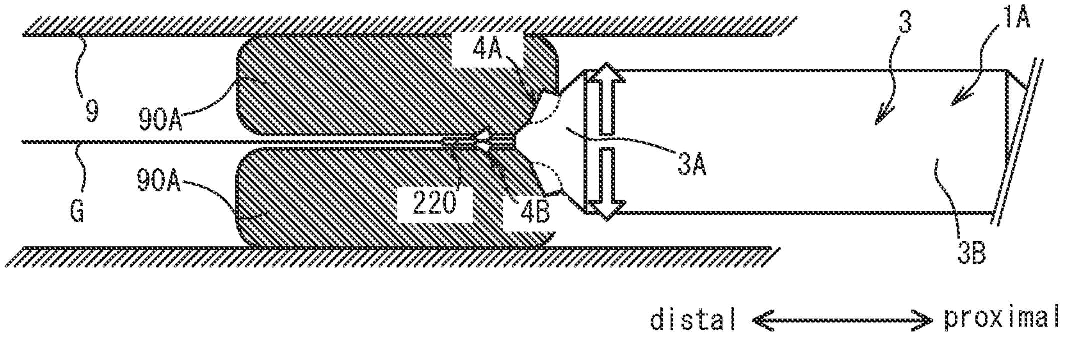
FIG. 3C is a view illustrating a usage example of the balloon catheter.

Next, the compressed fluid starts to be supplied to the balloon 3 so that the balloon 3 comes to be in the inflated state, as shown in FIG. 3C. The protruding portion 4A provided on the distal end connecting portion 3A digs into the interior wall of the stenotic lesion 90A. The balloon 3 dilates the area near the proximal end portion of the lumen of the stenotic lesion 90A with the distal end connecting portion 3A. Note that because the distal end connecting portion 3A increases in diameter toward the proximal side, a force in the proximal direction acts on the balloon 3 from the stenotic lesion 90A as the balloon 3 changes to the inflated state. However, because the protruding portion 4A digs into the stenotic lesion 90A, movement of the balloon 3 toward the proximal side is suppressed. Furthermore, the balloon 3 is inhibited from being pushed back toward the proximal side because the protruding portion 4B catches on the lumen of the stenotic lesion 90A.

Figure 3D:
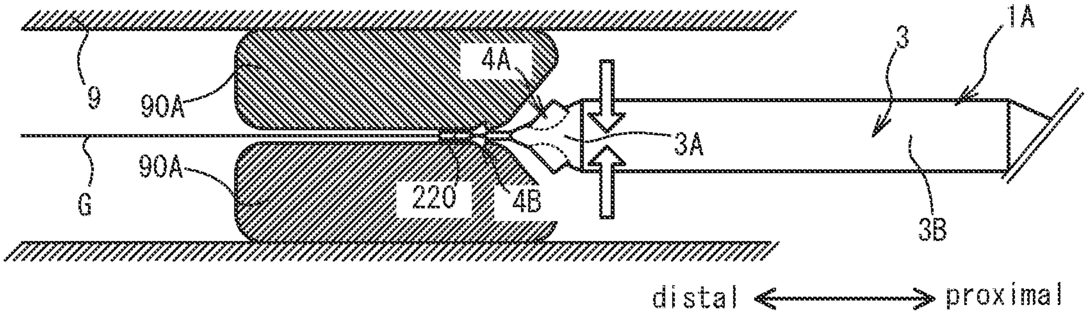
FIG. 3D is a view illustrating a usage example of the balloon catheter.
Figure 3E:
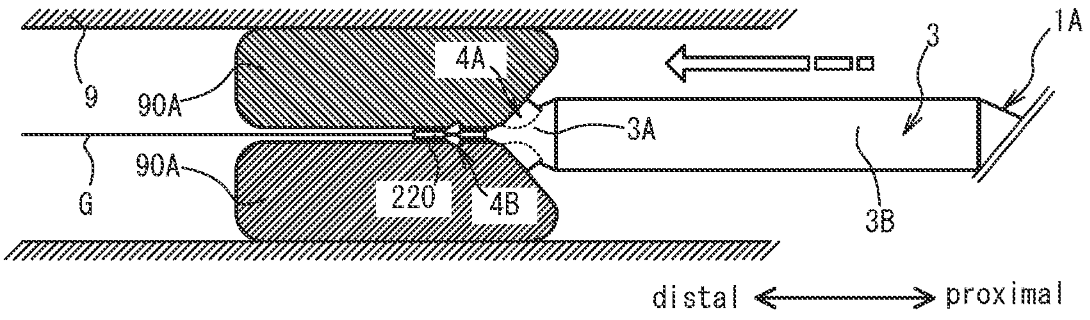
FIG. 3E is a view illustrating a usage example of the balloon catheter.

Next, the supplied compressed fluid is removed so that the balloon 3 comes to be in the deflated state, as shown in FIG. 3D. Next, the balloon catheter 1A moves distally by the proximal end being operated as shown in FIG. 3E. The distal end connecting portion 3A of the balloon 3 enters deeper into the lumen from the dilated proximal end portion of the stenotic lesion 90A. Then, movement of the balloon catheter 1A is stopped.

Figure 4A:
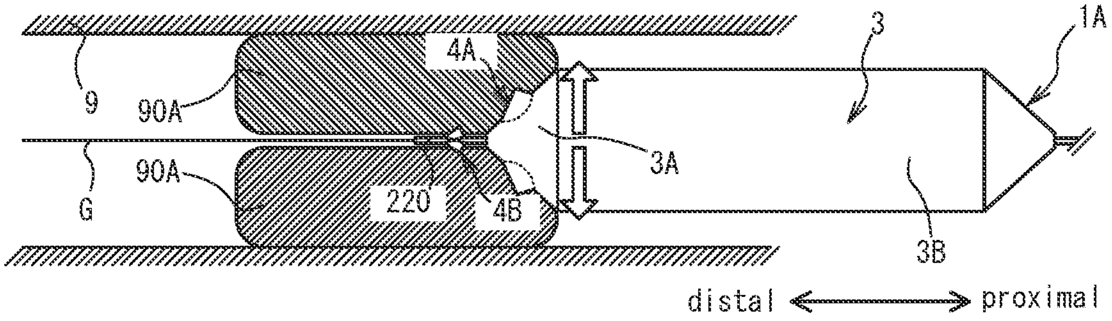
FIG. 4A is a view illustrating a usage example of the balloon catheter.

Next, the compressed fluid starts to be supplied into the balloon 3 so that the balloon 3 comes to be in the inflated state, as shown in FIG. 4A. The protruding portion 4A provided on the distal end connecting portion 3A digs into the interior wall of the stenotic lesion 90A. The balloon 3 dilates a portion of the stenotic lesion 90A distal to the portion dilated in FIGS. 3C and 3D using the distal end connecting portion 3A. Also, the balloon 3 dilates the portion of the stenotic lesion 90A dilated in FIGS. 3C and 3D with the inflatable portion 3B. As a result, an even wider portion of the lumen of the stenotic lesion 90A is dilated by the balloon 3. Note that the protruding portion 4A digs into the stenotic lesion 90A and the protruding portion 4B catches on the lumen of the stenotic lesion 90A. Therefore, movement of the balloon 3 toward the proximal side is inhibited even if force toward the proximal side acts on the balloon 3 in response to the balloon 3 changing to the inflated state.

Figure 4B:
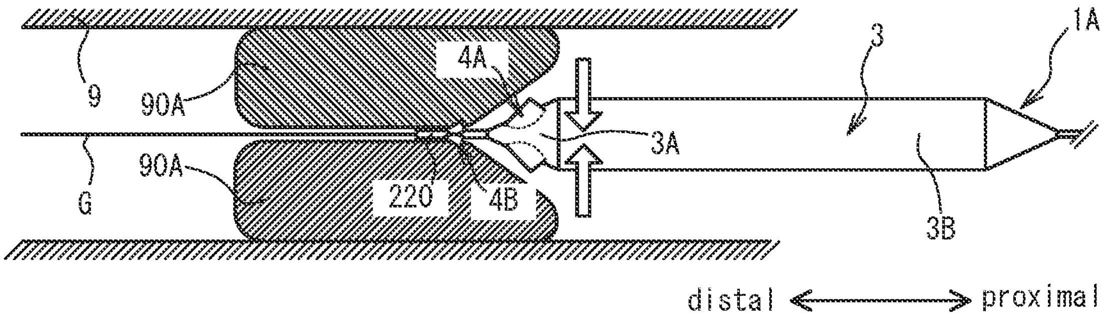
FIG. 4B is a view illustrating a usage example of the balloon catheter.

Next, the supplied compressed fluid is removed from the balloon 3 so that the balloon 3 comes to be in the deflated state, as shown in FIG. 4B.

Figure 4C:
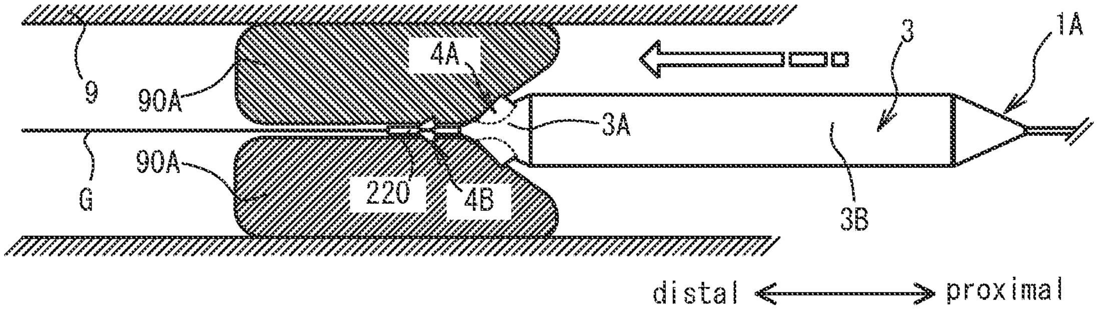
FIG. 4C is a view illustrating a usage example of the balloon catheter.
Figure 4D:
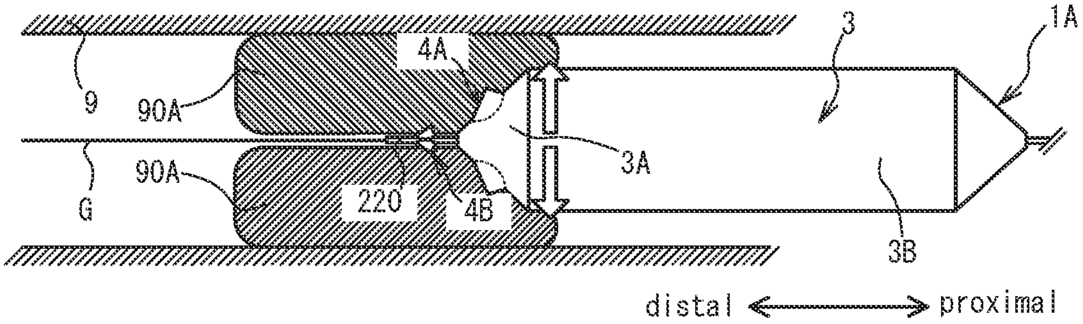
FIG. 4D is a view illustrating a usage example of the balloon catheter.
Figure 4E:
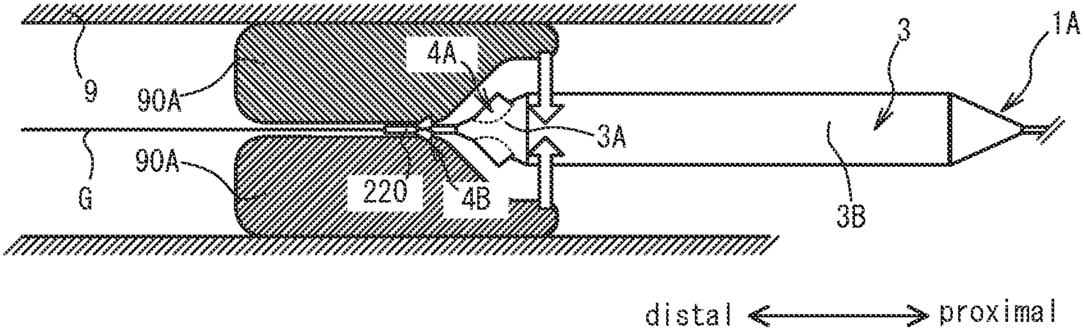
FIG. 4E is a view illustrating a usage example of the balloon catheter.
Figure 5A:
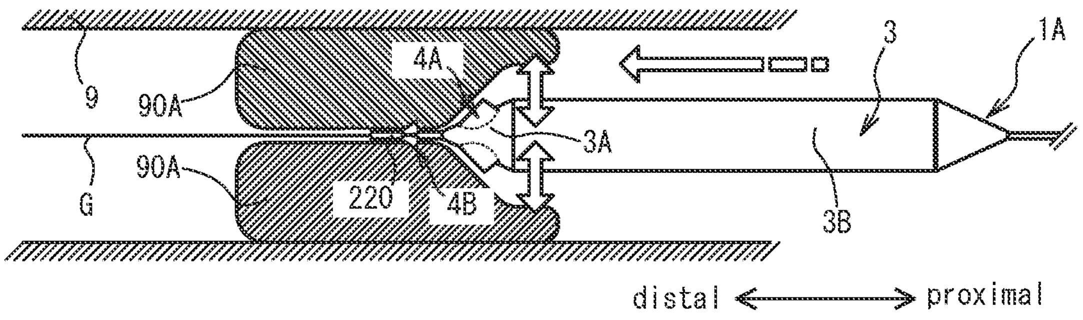
FIG. 5A is a view illustrating a usage example of the balloon catheter.
Figure 5B:
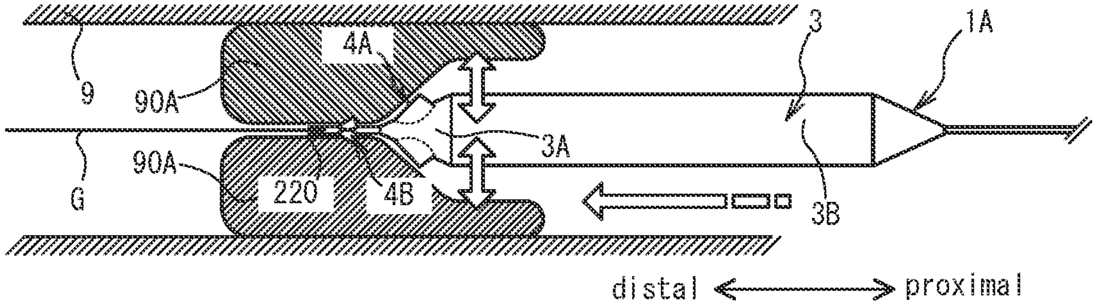
FIG. 5B is a view illustrating a usage example of the balloon catheter.
Figure 5C:
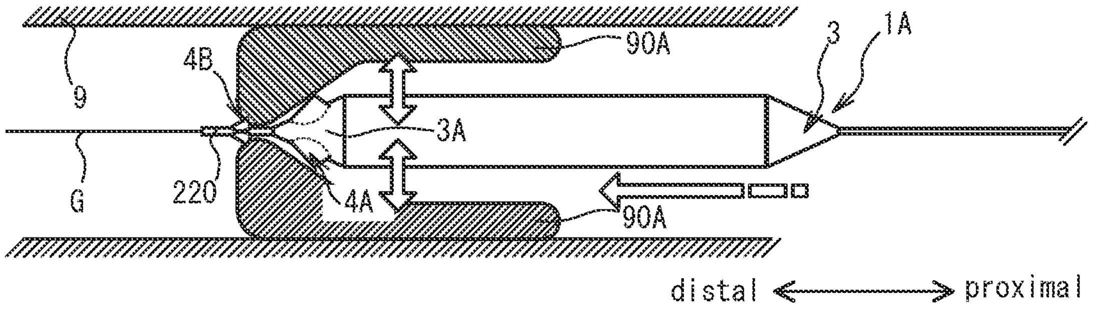
FIG. 5C is a view illustrating a usage example of the balloon catheter.
Figure 5D:
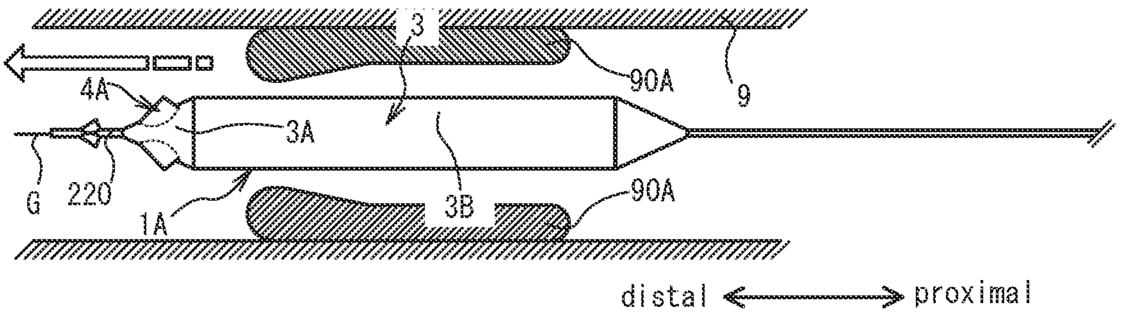
FIG. 5D is a view illustrating a usage example of the balloon catheter.

The same procedure as described above is repeatedly executed (FIG. 4C, FIG. 4D, FIG. 4E). Consequently, the balloon 3 of the balloon catheter 1A gradually moves toward the distal side through the lumen of the stenotic lesion 90A. The lumen of the stenotic lesion 90A gradually becomes larger from the area near the proximal end portion toward the distal side, as shown in FIG. 5A, FIG. 5B, and FIG. 5C. Finally, the lumen of the stenotic lesion 90A is dilated over the entire area by the balloon 3, as shown in FIG. 5D.

Then, the proximal end portion of the balloon catheter 1A is operated so that the balloon catheter 1A moves proximally. The procedure is completed by the balloon catheter 1A being pulled out from the blood vessel 9.

Operations and Effects of First Embodiment

The balloon catheter 1A can dilate the stenotic lesion 90A having a small lumen by gradually advancing the balloon 3 distally while repeatedly changing the balloon 3 between the inflated state and the deflated state. Here, the balloon catheter 1A is provided with the protruding portion 4A on the distal end connecting portion 3A of the balloon 3, and the protruding portion 4B on the distal end extending portion 220 of the inner tube 22. The protruding portions 4A and 4B inhibit the balloon 3 from moving proximally even if force toward the proximal side is received from the stenotic lesion 90A when the balloon 3 inflates. Therefore, the balloon catheter 1A can suitably dilate even the stenotic lesion 90A having a small lumen by performing an operation that gradually moves the balloon 3 distally while repeatedly changing the balloon 3 between the inflated state and the deflated state.

The distal end connecting portion 3A of the balloon 3 includes the regions W1 and W2 where the protruding portion 4A is not provided. Therefore, the size of the region of the distal end connecting portion 3A where the protruding portion 4A is provided is smaller than it is when the protruding portion 4A is provided across the entire region in the extending direction of the distal end connecting portion 3A. Also, the distal end extending portion 220 of the inner tube 22 includes the regions W3 and W4 where the protruding portion 4B is not provided. Therefore, the size of the region of the distal end extending portion 220 where the protruding portion 4B is provided is smaller than it is when the protruding portion 4B is provided across the entire region in the extending direction of the distal end extending portion 220. Therefore, the balloon catheter 1A makes it possible to achieve excellent passablity of the balloon 3 through the blood vessel 9 compared to when the protruding portions 4A and 4B are provided along the entire region of the distal end connecting portion 3A and the distal end extending portion 220.

The balloon catheter 1A enables the protruding portion 4A provided on the distal end connecting portion 3A of the balloon 3 to dig into the stenotic lesion 90A in the process of repeatedly inflating and deflating the balloon 3 to dilate the stenotic lesion 90A in the blood vessel 9. In this case, the balloon 3 can be inhibited from moving backward proximally even if the balloon 3 receives proximal force from the stenotic lesion 90A when the balloon 3 is inflating. Therefore, because the balloon catheter 1A can inflate the balloon 3 while gradually advancing the balloon 3 with respect to the stenotic lesion 90A having a small lumen, the balloon catheter 1A is able to efficiently dilate the stenotic lesion 90A having a small lumen.

With the protruding portion 4A, the angle $\theta 12$ of the proximal end inclined portion 412 with respect to the distal end connecting portion 3A is greater than the angle $\theta 11$ of the distal end inclined portion 411 with respect to the distal end connecting portion 3A. In this case, the resistance force that the protruding portion 4A receives from the stenotic lesion 90A when the balloon 3 enters the lumen of the stenotic lesion 90A can be suppressed. Therefore, the balloon catheter 1A can reduce the possibility of the balloon 3 being pushed back proximally by the resistance force from the stenotic lesion 90A during the process of the balloon 3 entering the stenotic lesion 90A.

The protruding portion 4B provided on the distal end extending portion 220 of the balloon 3 catches on the stenotic lesion 90A when the balloon 3 moves in the direction opposite the entering direction inside the blood vessel 9. Therefore, with the balloon catheter 1A, the protruding portion 4B of the distal end extending portion 220 can inhibit the balloon 3 from being pushed back proximally when repeatedly inflating and deflating the balloon 3 to dilate the stenotic lesion 90A inside the blood vessel 9.

With the protruding portion 4B, the angle θ22 of the proximal end inclined portion 422 with respect to the distal end extending portion 220 is greater than the angle θ21 of the distal end inclined portion 421 with respect to the distal end extending portion 220. In this case, the balloon catheter 1A can reduce the possibility of the protruding portion 4B catching on the blood vessel 9 and thus being impeded from advancing when the balloon 3 is advanced inside the blood vessel 9.

Special Notes Relating to First Embodiment

The shape, number, and arrangement of the protrusions of the protruding portions 4A and 4B are not limited to those in the foregoing embodiment. For example, the number of protrusions of the protruding portions 4A and 4B may be one or three or more. Also, if the number of protrusions is three or more, the three or more protrusions may be arranged in the circumferential direction around the center axis C1. The shape of the protrusions of the protruding portions 4A and 4B may be a pyramid, a truncated cone, a truncated pyramid, etc., or a prism. Note that if the shape of the protrusions 41A and 42A of the protruding portion 4A is a triangular prism, one of the side surfaces may connect to the distal end connecting portion 3A of the balloon 3, and the remaining two side surfaces may form the distal end inclined portion 411 and the proximal end inclined portion 412, and the intersection of the remaining two side surfaces may form the apex 410. Similarly, if the shape of the protrusions 41B and 42B of the protruding portion 4B is a triangular prism, one of the side surfaces may connect to the distal end extending portion 220 of the inner tube 22, and the remaining two side surfaces may form the distal end inclined portion 421 and the proximal end inclined portion 422, and the intersection of the remaining two side surfaces may form the apex 420.

The plurality of protrusions of the protruding portion 4A may be arranged in the extending direction along the distal end connecting portion 3A of the balloon 3. For example, the plurality of protrusions may be arranged along each of a plurality of virtual lines extending in the radial direction from the center axis C1 when the balloon 3 is viewed from the distal end side. At this time, the protrusion amount of each of the plurality of protrusions need not be the same. For example, the protrusion amount of each of the plurality of protrusions may be defined according to the distance from the center axis C1.

A first connecting portion that connects the protrusions 41A and 41B may be provided. A second connecting portion that connects the protrusions 42A and 42B may be provided. The first connecting portion and the second connecting portion may protrude outward from the outer surface of the distal end connecting portion 3A of the balloon 3 and the outer surface of the distal end extending portion 220 of the inner tube 22, respectively. That is, the protrusions 41A and 41B and the protrusions 42A and 42B may each be integrated to form a single protrusion.

The position in the extending direction of the proximal end portion 416 of each of the protrusions 41A and 42A of the protruding portion 4A may coincide with the portion of the distal end connecting portion 3A that connects with the distal end portion 30D of the inflatable portion 3B. Alternatively, the position in the extending direction of the distal end portion 415 of each of the protrusions 41A and 42A of the protruding portion 4A may coincide with the distal end portion 3D of the distal end connecting portion 3A.

The protrusions 41B and 42B of the protruding portion 4B may each be provided from the distal end portion 221 of the inner tube 22 of the distal end extending portion 220 to the portion of the distal end extending portion 220 where the distal end portion 3D of the distal end connecting portion 3A is connected. The position of the distal end portion 425 of each of the protrusions 41B and 42B may coincide with the position of the distal end portion 221 of the inner tube 22. The proximal end portion 426 of each of the protrusions 41B and 42B may coincide with the position of the distal end portion 3D of the distal end connecting portion 3A. That is, the protruding portion 4B may be provided over the entire area in the extending direction on the distal end extending portion 220 of the inner tube 22. In this case, the regions W3 and W4 where the protruding portion 4B is not provided in the extending direction of the distal end extending portion 220 of the inner tube 22 need not be provided.

The balloon catheter 1A may have only one of the protrusions 4A or 4B. For example, the balloon catheter 1A may only have the protruding portion 4A and not have the protruding portion 4B. Alternatively, the balloon catheter 1A may only have the protruding portion 4B and not have the protruding portion 4A.

In the protruding portion 4A, the angle θ11 of the distal end inclined portion 411 with respect to the distal end connecting portion 3A and the angle θ12 of the proximal end inclined portion 412 with respect to the distal end connecting portion 3A may be the same, or the angle θ11 may be greater than the angle θ12. One of the angle θ11 or the angle θ12 may be orthogonal to the distal end connecting portion 3A. In the protruding portion 4B, the angle θ21 of the distal end inclined portion 421 with respect to the distal end extending portion 220 and the angle θ22 of the proximal end inclined portion 422 with respect to the distal end extending portion 220 may be the same, or the angle θ21 may be greater than the angle θ22. One of the angle θ21 or the angle θ22 may be orthogonal to the distal end extending portion 220.

A first protruding portion having a protrusion amount smaller than the protrusion amount of the protruding portion 4A may be provided in the regions W1 and W2 of the distal end connecting portion 3A of the balloon 3. Also, a second protruding portion having a protrusion amount smaller than the protrusion amount of the protruding portion 4B may be provided in the regions W3 and W4 of the distal end extending portion 220. The ratio of the protrusion amount of the first protruding portion to the protrusion amount of the protruding portion 4A, and the ratio of the protrusion amount of the second protruding portion to the protrusion amount of the protruding portion 4B are not particularly limited, and may be, for example, 50% or less, and more preferably, 10% or less.

When the balloon catheter 1A only has the protruding portion 4B and the first protruding portion is provided, the first protruding portion may be provided on the entire region between the distal end portion 3D and the portion of the distal end connecting portion 3A of the balloon 3 where the distal end portion 30D of the inflatable portion 3B is connected. Also, the protrusion amount of the first protruding portion may be less than the protrusion amount of the protruding portion 4B.

When the balloon catheter 1A only has the protruding portion 4A and the second protruding portion is provided, the second protruding portion may be provided on the entire region between the distal end portion 221 and the portion of the distal end extending portion 220 where the distal end portion 3D of the balloon 3 is connected. Also, the protrusion amount of the second protruding portion may be less than the protrusion amount of the protruding portion 4A.

Second Embodiment (Balloon Catheter 1B)

Figure 6:
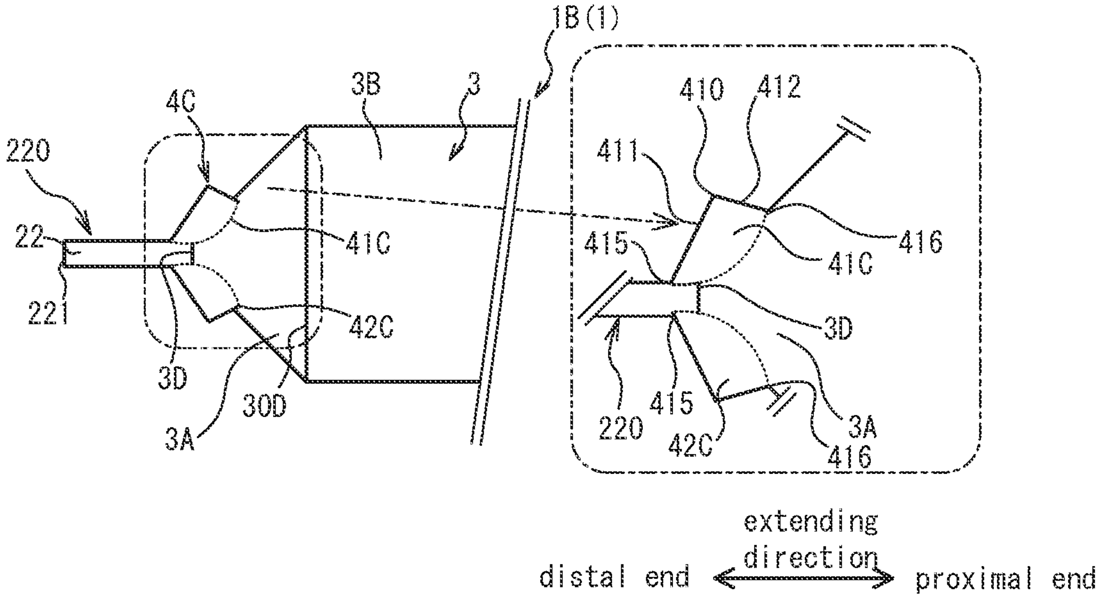
FIG. 6 is an enlarged view of an area near a distal end connecting portion 3A of a balloon catheter.

The balloon catheter 1B will now be described with reference to FIG. 6. The balloon catheter 1B differs from the balloon catheter 1A in that it does not have the protruding portion 4B, and has a protruding portion 4C instead of the protruding portion 4A. Hereinafter, a description of the structure of the balloon catheter 1B that is the same as that of the balloon catheter 1A will be omitted.

The protruding portion 4C has protrusions 41C and 42C that have the same shape as the protrusions 41A and 41B of the protruding portion 4A. The protrusions 41C and 42C are provided on a portion of the outer surface of the distal end connecting portion 3A of the balloon 3 that includes the distal end portion 3D. In this case, a portion on the distal end side of each of the protrusions 41C and 42C is provided on the outer surface of the distal end extending portion 220 of the inner tube 22, and a portion on the proximal end side of each of the protrusions 41C and 42C is provided on the outer surface of the distal end connecting portion 3A of the balloon 3. Also, the distal end portion 415 of each of the protrusions 41C and 42C is positioned on the distal end side of the distal end portion 3D of the distal end connecting portion 3A of the balloon 3, and the proximal end portion 416 of each of the protrusions 41C and 42C is positioned on the proximal end side of the distal end portion 3D of the distal end connecting portion 3A of the balloon 3.

Operations and Effects of Second Embodiment

With the balloon catheter 1B, the balloon 3 inflates to dilate the stenotic lesion 90A when the distal end portion 3D of the balloon 3 has entered the stenotic lesion 90A in the blood vessel 9. In this case, the protruding portion 4C can inhibit the balloon 3 from being pushed back in the direction opposite the advancing direction even if the region where the balloon catheter 1B enters the stenotic lesion 90A is extremely small. Therefore, even if the stenotic lesion 90A is hard and it is difficult to get the distal end connecting portion 3A of the balloon 3 in the deflated state to enter the lumen, the balloon catheter 1B can dilate the stenotic lesion 90A by repeatedly inflating and deflating the balloon 3.

Special Notes Relating to Second Embodiment

In addition to the protruding portion 4C, the protruding portion 4A according to the first embodiment may also be provided on the distal end connecting portion 3A. Also, in addition to the protruding portion 4C, the protruding portion 4B according to the first embodiment may also be provided on the distal end extending portion 220.

Third Embodiment (Balloon Catheter 1C)

Figure 7:
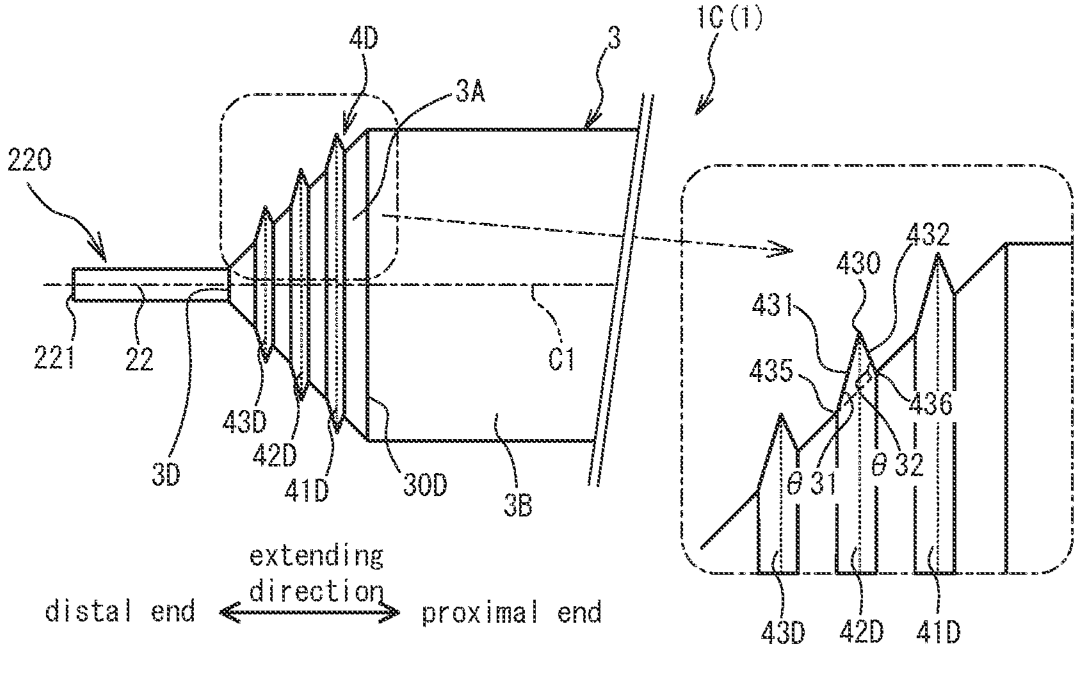
FIG. 7 is an enlarged view of an area near the distal end connecting portion 3A of a balloon catheter.

The balloon catheter 1C will now be described with reference to FIG. 7. The balloon catheter 1C differs from the balloon catheter 1A in that it does not have the protruding portion 4B, and has a protruding portion 4D instead of the protruding portion 4A. Hereinafter, a description of the structure of the balloon catheter 1C that is the same as that of the balloon catheter 1A will be omitted.

The protruding portion 4D has protrusions 41D, 42D, and 43D. The protrusions 41D to 43D are provided on the outer surface of the distal end connecting portion 3A of the balloon 3 and protrude outward. The protrusions 41D to 43D each have an annular shape that extends in the circumferential direction around the center axis C1. The protrusions 41D, 42D, and 43D are arranged in that order toward the distal end side. The diameter of each of the protrusions 41D, 42D, and 43D about the center axis C1 gradually becomes smaller in the order of the protrusions 41D, 42D, and 43D.

The protrusions 41D to 43D each have a planar-shaped distal end inclined portion 431 and a planar-shaped proximal end inclined portion 432 that extend outward from the outer surface of the distal end connecting portion 3A. Hereinafter, the protrusion 42D will be described as an example.

The portion near the distal end portion 3D of the distal end connecting portion 3A, of the portion of the protrusion 42D that is connected to the distal end connecting portion 3A, will be referred to as a distal end portion 435. The distal end inclined portion 431 extends inclined with respect to the radial direction from the distal end portion 435 toward the proximal end side. The portion near the distal end portion 30D of the inflatable portion 3B, of the portion of the protrusion 42D that is connected to the distal end connecting portion 3A will be referred to as a proximal end portion 436. The proximal end inclined portion 432 extends inclined with respect to the radial direction from the proximal end portion 436 toward the distal end side. The end portion of the distal end inclined portion 431 on the side opposite the distal end portion 435 and the end portion of the proximal end inclined portion 432 on the side opposite the proximal end portion 436 are connected at an apex 430. The angle θ32 of the proximal end inclined portion 432 with respect to the distal end connecting portion 3A is greater than the angle θ31 of the distal end inclined portion 431 with respect to the distal end connecting portion 3A.

Operations and Effects of Third Embodiment

With the balloon catheter 1C, the protruding portion 4D is able to dig into the stenotic lesion 90A over a wide area in the circumferential direction at the distal end connecting portion 3A. Therefore, with the balloon catheter 1C, the protruding portion 4D can inhibit the balloon 3 from moving in the direction opposite the direction of entry into the stenotic lesion 90A when the balloon 3 inflates.

Special Notes Relating to Third Embodiment

The number and shape of the protrusions of the protruding portion 4D are not limited to those of the foregoing embodiment. For example, the apex 430 of each of the protrusions 41D to 43D may be curved outward in a protruding shape. An annular protruding portion extending in the circumferential direction around the center axis C1 may also be provided on the distal end extending portion 220 of the inner tube 22. The connecting portion that connects the protrusions 41D to 43D may extend in the extending direction along the outer surface of the distal end connecting portion 3A.

Fourth Embodiment (Balloon Catheter 1D)

Figure 8:
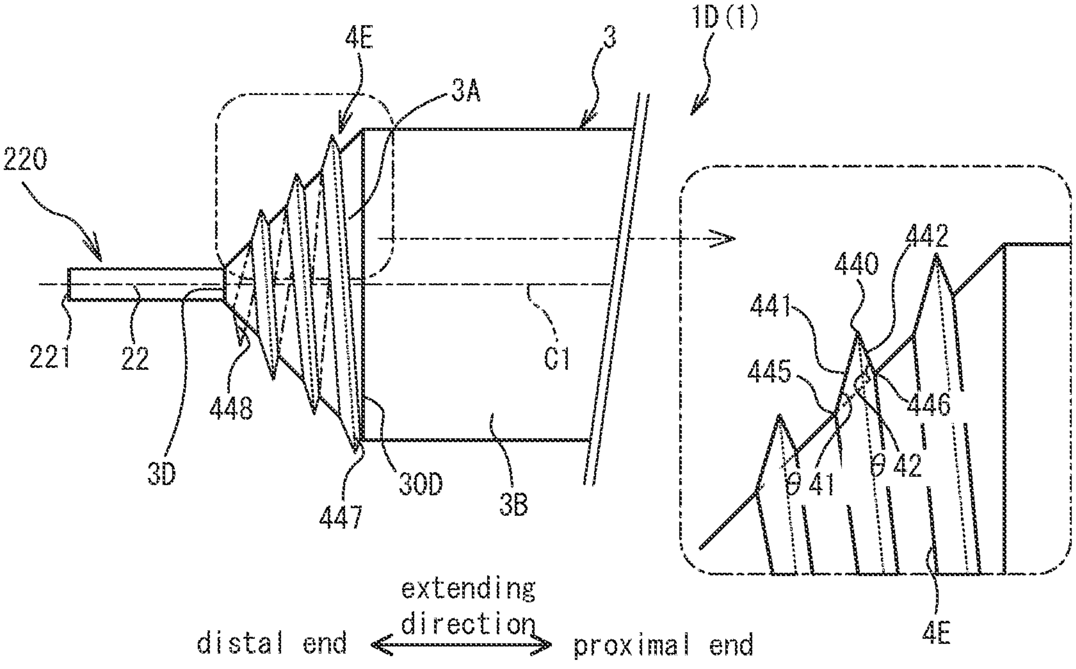
FIG. 8 is an enlarged view of an area near the distal end connecting portion 3A of a balloon catheter.

The balloon catheter 1D will now be described with reference to FIG. 8. The balloon catheter 1D differs from the balloon catheter 1C in that it has a protruding portion 4E instead of the protruding portion 4D. Hereinafter, a description of the structure of the balloon catheter 1D that is the same as that of the balloon catheter 1C will be omitted.

The protruding portion 4E is provided on the outer surface of the distal end connecting portion 3A of the balloon 3 and protrudes outward. The protruding portion 4E has a spiral shape that extends in the circumferential direction around the center axis C1. An end portion 447 on the proximal end side of the protruding portion 4E is positioned near the distal end side with respect to the distal end portion 30D of the inflatable portion 3B of the balloon 3. An end portion 448 on the distal end side of the protruding portion 4E is positioned near the proximal end side with respect to the distal end portion 3D of the distal end connecting portion 3A.

The portion near the distal end portion 3D of the distal end connecting portion 3A, of the portion of the protruding portion 4E that is connected to the distal end connecting portion 3A will be referred to as a distal end portion 445. The planar-shaped portion extending inclined with respect to the radial direction from the distal end portion 445 toward the proximal end side will be referred to as a distal end inclined portion 44I. The portion near the distal end portion 30D of the inflatable portion 3B, of the portion of the protruding portion 4E that is connected to the distal end connecting portion 3A will be referred to as a proximal end portion 446. The planar-shaped portion extending inclined with respect to the radial direction from the proximal end portion 446 toward the distal end side will be referred to as a proximal end inclined portion 442. The end portion of the distal end inclined portion 441 on the side opposite the distal end portion 445 and the end portion of the proximal end inclined portion 442 on the side opposite the proximal end portion 446 are connected at an apex 440. The angle θ42 of the proximal end inclined portion 442 with respect to the distal end connecting portion 3A is greater than the angle θ41 of the distal end inclined portion 441 with respect to the distal end connecting portion 3A.

Operations and Effects of Fourth Embodiment

The balloon catheter 1D can apply the protruding portion 4E to the stenotic lesion 90A over a wide area in the extending direction and the circumferential direction of the distal end connecting portion 3A. Therefore, with the balloon catheter 1D, the protruding portion 4E can inhibit the balloon 3 from moving in the direction opposite the direction of entry into the stenotic lesion 90A when the balloon 3 inflates.

Special Notes Relating to Fourth Embodiment

The shape of the protruding portion 4E is not limited to that of the foregoing embodiment. For example, the apex 440 of the protruding portion 4E may be curved outward in a protruding shape. A spiral-shaped protruding portion that extends in the circumferential direction around the center axis C1 may also be provided on the distal end extending portion 220 of the inner tube 22.

Fifth Embodiment (Balloon Catheter 1E)

Figure 9:
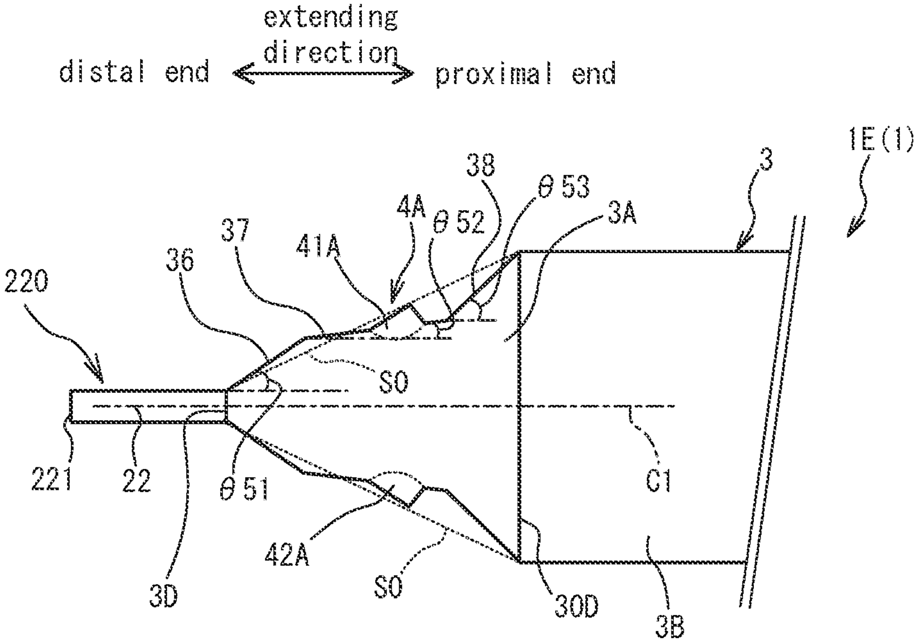
FIG. 9 is an enlarged view of an area near the distal end connecting portion 3A of a balloon catheter.

The balloon catheter 1E will now be described with reference to FIG. 9. The balloon catheter 1E differs from the balloon catheter 1A in that the protruding portion 4B is not provided on the distal end extending portion 220. Also, the shape of the distal end connecting portion 3A of the balloon 3 differs from that of the balloon catheter 1A. Hereinafter, a description of the structure of the balloon catheter 1E that is the same as that of the balloon catheter 1A will be omitted.

The distal end connecting portion 3A of the balloon 3 has inclined portions 36, 37, and 38. When the balloon 3 is in the inflated state, the inclined portion 36 extends while increasing in diameter from the distal end portion 3D of the distal end connecting portion 3A toward the proximal end side. The inclined portion 37 extends while increasing in diameter from the end portion of the inclined portion 36 on the side opposite the end portion of the inclined portion 36 that is connected to the distal end portion 3D in the extending direction toward the proximal end side. The inclined portion 38 extends while increasing in diameter from the end portion of the inclined portion 37 on the side opposite the end portion of the inclined portion 37 that is connected to the inclined portion 36 in the extending direction toward the proximal end side.

With regards to the inclined portions 36 to 38, the angles formed between the extending direction and the direction extending from the end portion near the distal end portion 3D toward the end portion near the distal end portion 30D are defined as the inclination angles. The inclination angle of the inclined portion 36 is denoted θ51, the inclination angle of the inclined portion 37 is denoted θ52, and the inclination angle of the inclined portion 38 is denoted θ53. In this case, the inclination angles θ51, θ52, and θ53 are different from each other. The inclination angles θ51 to θ53 have a magnitude relationship of θ52<θ51<θ53. The inclination angle θ53 is the largest and the inclination angle θ52 is the smallest.

The shape of the protrusions 41A and 42A of the protruding portion 4A is the same as it is in the balloon catheter 1A. The protrusions 41A and 42A are provided on the inclined portion 37 which has the smallest inclination angle θ52 of the inclined portions 36 to 38.

A virtual plane S0 that connects the distal end portion 30D of the inflatable portion 3B of the balloon 3 and the distal end portion 3D of the balloon 3 is defined. In this case, the protrusions 41A and 42A are positioned on the side of the virtual plane S0 near the center axis C1, i.e., to the inside with respect to the virtual plane S0.

Operations and Effects of Fifth Embodiment

When the balloon 3 inflates, the inclined portions 36 to 38 of the distal end connecting portion 3A move in a direction orthogonal to each other. Here, the moving direction of the inclined portion 37 having the relatively small inclination angle θ52 approximates the radial direction more than the moving direction of the inclined portions 36 and 38 that have relatively large inclination angles θ51 and θ53 does. Note that the protruding portion 4A more easily digs into the stenotic lesion 90A of the blood vessel 9 the closer the moving direction of the protruding portion 4A when the balloon 3 inflates is to the radial direction.

With the balloon catheter 1E, the protruding portion 4A is provided on the inclined portion 37 having the relatively small inclination angle θ52. When the balloon 3 inflates, the protruding portion 4A moves in a direction orthogonal to the inclined portion 37. Note that the inclination angle θ52 is defined as the angle of the inclined portion 37 with respect to the extending direction, so when the inclination angle θ52 is small, the angle between the direction orthogonal to the inclined portion 37, i.e., the moving direction of the protruding portion 4A when the balloon 3 inflates, and the radial direction orthogonal to the extending direction is also small.

That is, the protruding portion 4A moves in a direction approximating the radial direction when the balloon 3 inflates. Therefore, the balloon catheter 1E enables the protruding portion 4A to suitably dig into the stenotic lesion 90A when the balloon 3 inflates.

Special Notes Relating to Fifth Embodiment

The shape of the protruding portion 4A provided on the inclined portion 37 is not limited to that of the foregoing embodiment. For example, the protruding portion may have the shape (annular shape) of the protruding portion 4D in the third embodiment, or the shape (spiral shape) of the protruding portion 4E in the fourth embodiment. The inclination angles θ51 and θ53 may be the same. The number of inclined portions of the distal end connecting portion 3A is not limited to three, and may be two or four or more. If there are three or more inclined portions, protruding portions may be provided on a plurality of the inclined portions having an inclination angle less than a predetermined threshold value. The protruding portion 4A may protrude outward with respect to the virtual plane S0.

Sixth Embodiment (Balloon Catheter 1F)

Figure 10:
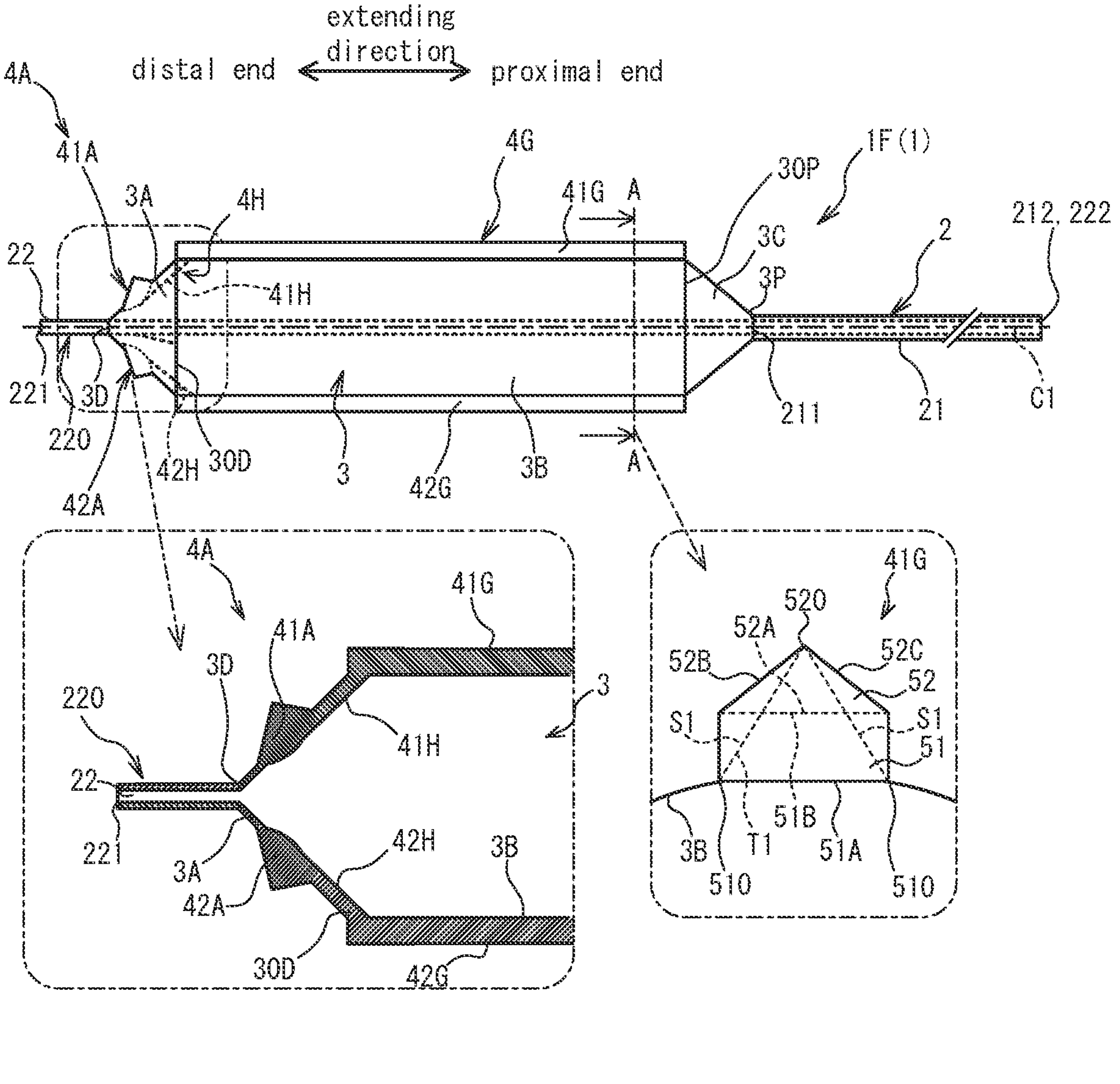
FIG. 10 is a view of a balloon catheter 1F from the side, and a sectional view of the balloon catheter taken along line A-A from the direction of the arrow.

The balloon catheter 1F will now be described with reference to FIG. 10. The balloon catheter 1F differs from the balloon catheter 1A in that it has protruding portions 4G and 4H in addition to the protruding portion 4A, but does not have the protruding portion 4B. Hereinafter, a description of the structure of the balloon catheter 1F that is the same as that of the balloon catheter 1A will be omitted.

The protruding portion 4G is provided on the outer surface of the inflatable portion 3B of the balloon 3 and protrudes outward. The protruding portion 4G has protrusions 41G and 42G. The protrusions 41G and 42G both extend in the extending direction between the proximal end portion 30P and the distal end portion 30D of the inflatable portion 3B. The protrusions 41G and 42G face each other across the center axis C1. The positions of the protrusions 41A and 41G in the circumferential direction coincide. The positions of the protrusions 42A and 42G in the circumferential direction coincide.

The shape of the protrusions 41G and 42G is the same. Hereinafter, the shape will be described giving the protrusion 41G as an example. The protrusion 41G has a base portion 51 and a tip end portion 52. The shape of the base portion 51 is a quadratic prism, extending in the extending direction. A side surface 51A of the base portion 51 is connected to the outer surface of the inflatable portion 3B of the balloon 3. The shape of the tip end portion 52 is a triangular prism, extending in the extending direction. A side surface 52A of the tip end portion 52 is connected to a side surface 51B of the base portion 51 that is opposite to the side surface 51A. Side surfaces 52B and 52C of the tip end portion 52 other than the side surface 52A are connected to an apex 520. The distance between the side surfaces 51A and 52B of the base portion 51, and the distance between the apex 520 and the side surface 52A of the tip end portion 52 are equal.

In a cross-section of the protrusion 41G, both end portions 510 of the side surface 51A in a direction orthogonal to the extending direction are defined. Also, two virtual line segments S1 connecting each of the end portions 510 and the apex 520 are defined. In this case, a portion of each of the tip end portion 52 and the base portion 51 of the protrusion 41G is arranged to the outside of a virtual triangle (hereinafter, referred to as a virtual triangle T1) defined by the two virtual line segments S1 and the side surface 51A.

The protruding portion 4H is provided on an inner surface of the distal end connecting portion 3A of the balloon 3 and protrudes inward. The protruding portion 4H has protrusions 41H and 42H. The protruding portion 41H extends between the protrusion 41A and the end portion on the distal end side of the protrusion 41G. The protrusion 42H extends between the protrusion 42A and the end portion on the distal end side of the protrusion 42G. The protruding portion 4H is interposed between the protruding portions 4A and 4G and connects the protruding portions 4A and 4G inside the balloon 3.

Operations and Effects of Sixth Embodiment

With the balloon catheter 1F, the rigidity of the portion where the protruding portion 4H is provided on the balloon 3 can be equal to the rigidity of the portion of the balloon 3 where the protruding portion 4A is provided. Therefore, the protruding portion 4H can inhibit the balloon 3 from being pushed back in the direction toward the center axis C1 due to the protruding portion 4A receiving force from the stenotic lesion 90A when the balloon 3 inflates. The protruding portion 4H protrudes inward from the inner surface of the distal end connecting portion 3A of the balloon 3, and does not protrude outward from the outer surface of the distal end connecting portion 3A of the balloon 3. Therefore, the balloon catheter 1F can inhibit a decrease in passability of the balloon 3 due to the provision of the protruding portion 4H.

When the balloon 3 deflates, an inward force acts on the portion of the balloon 3 where the protruding portion 4H is provided. In this case, wings are more easily formed during the deflation process of the balloon 3. Note that the diameter of the balloon 3 in the deflated state is minimized by folding the wings formed in the deflated state. Therefore, in the balloon catheter 1F, the protruding portion 4H can suitably form wings in the balloon 3 in the deflated state, so the diameter of the balloon 3 in the deflated state can be reduced.

In a cross-section of the protrusions 41G and 42G of the protruding portion 4G, a portion of each of the base portion 51 and the tip end portion 52 is arranged to the outside of the virtual triangle T1. Therefore, the protrusions 41G and 42G will not easily fall down even if external force is applied. Consequently, with the balloon catheter 1F, when the balloon 3 inflates, not only the protruding portion 4A but also the protruding portion 4G can be applied to the stenotic lesion 90A, so the stenotic lesion 90A can be appropriately treated.

Special Notes Relating to Sixth Embodiment

A third protruding portion that protrudes outward may be provided on the outer surface of the portion of the distal end connecting portion 3A of the balloon 3 where the protruding portion 4H is provided on the inner surface. Note that the protrusion amount of the third protruding portion may be smaller than the protrusion amount of the protruding portion 4A. The ratio of the protrusion amount of the third protruding portion to the protrusion amount of the protruding portion 4A is not particularly limited, and is, for example, 50% or less, and more preferably, 10% or less.

Figure 11:
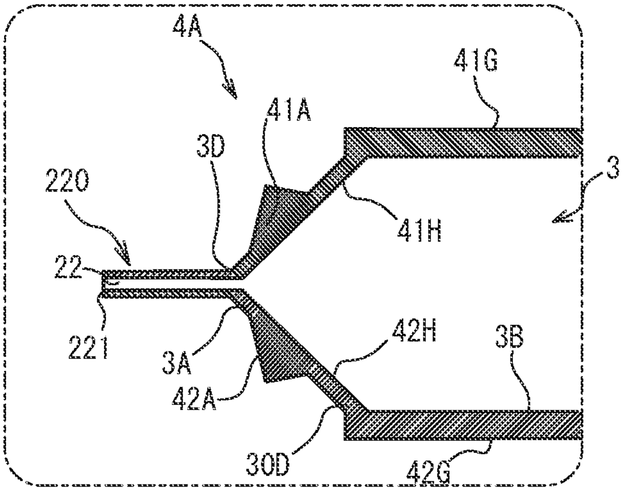
FIG. 11 is a view of a modified example of the balloon catheter.

As shown in FIG. 11, the protruding portion 4H may further extend between the end portion on the distal end side of the protruding portion 4G and the distal end portion 3D of the balloon 3. In this case, the protruding portion 4H may be provided between the distal end portion 3D of the balloon 3 and the end portion on the distal end side of the protruding portion 4G on the inner surface of the distal end connecting portion 3A of the balloon 3.

The protruding portion 4G may be provided on the inner surface of the inflatable portion 3B of the balloon 3 and protrude inward. The protruding portion 4G may be formed in an annular shape in the circumferential direction around the center axis C1. In this case, the protruding portion 4G may be formed only near the distal end portion 30D of the inflatable portion 3B of the balloon 3.

The protruding portion 4H may be provided on the entire region on the proximal end side of the protruding portion 4A in the extending direction, of the inner surface of the distal end connecting portion 3A of the balloon 3.

Figure 12A:
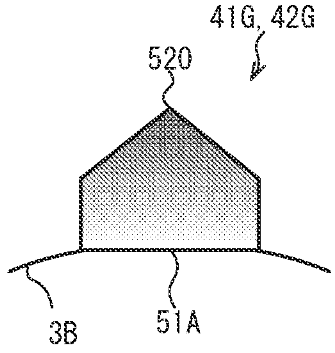
FIG. 12A is a view of a modified example of protrusions.

The hardness of each of the protrusions 41G and 42G of the protruding portion 4G may the uniform across the entire region or different for each portion. For example, as shown in FIG. 12A, the hardness of each of the protrusions 41G and 42G may become gradually harder from the side surface 51A toward the apex 520. In this case, the area of the protrusions 41G and 42G near the apex 520, in particular, will not easily fall down even if external force is applied, so the protruding portion 4G is able to appropriately dig into the stenotic lesion 90A when the balloon 3 inflates. Also, the area near the portion of the protrusions 41G and 42G that is connected to the balloon 3 can remain flexible. Therefore, it is possible to suppress a decrease in passability due to the protruding portion 4G catching on the interior wall when the balloon 3 passes through the blood vessel 9.

Figure 12B:
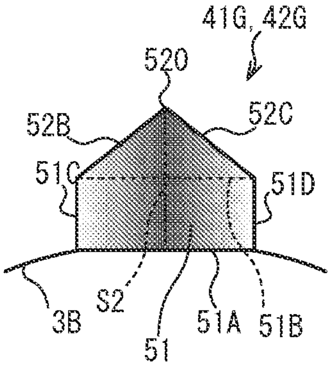
FIG. 12B is a view of the modified example of the protrusions.

For example, as shown in FIG. 12B, a virtual center S2 that is a virtual line segment that passes through the apex 520 and extends in the radial direction is defined for the protrusions 41G and 42G. Side surfaces 51C and 51D excluding the side surfaces 51A and 51B are defined for each base portion 51 of the protrusions 41G and 42G. In this case, the hardness of each of the protrusions 41G and 42G may become gradually harder from each of the side surfaces 51C, 51D, 52B, and 52C toward the virtual center S2. Also, for example, as shown in FIG. 12C, in a cross-section of the protrusions 41G and 42G, the hardness of the portion located inside the virtual triangle Tl may be higher than the hardness of the portion located outside the virtual triangle T1.

Figure 12C:
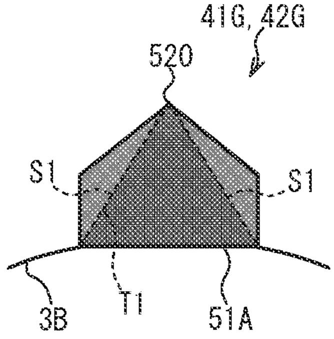
FIG. 12C is a view of the modified example of the protrusions.

In the case of the example shown in FIGS. 12B and 12C, the protruding portion 4G is stably arranged on the outer surface of the balloon 3, and so will not easily fall down even if external force is applied. Therefore, the protruding portion 4G is able to suitably dig into the stenotic lesion 90A when the balloon 3 inflates.

The shape of the protruding portion 4G is not limited to that of the foregoing embodiment. Modified examples (protrusions 46G (refer to FIG. 13A), 47G (refer to FIG. 13B), and 48G (refer to FIG. 13C)) relating to the shape of the protrusions 41G and 42G of the protruding portion 4G will now be described. Hereinafter, the direction passing through the apex 520 from the center axis C1 of the balloon 3 and extending in the radial direction will be referred to as a protruding direction. The direction orthogonal to the extending direction and orthogonal to the protruding direction will be referred to as an orthogonal direction.

Figure 13A:
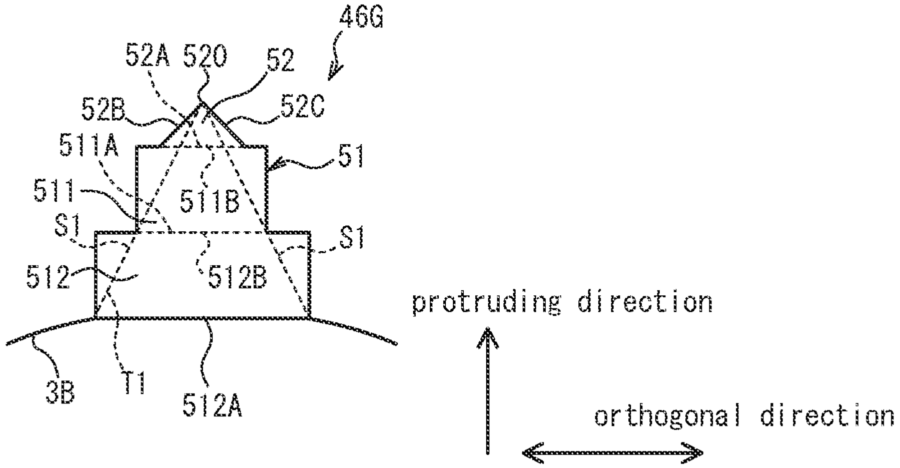
FIG. 13A is a view of a protrusion.

The protrusion 46G shown in FIG. 13A has, as the base portion 51, base elements 511 and 512. The shape of each of the base elements 511 and 512 is a quadratic prism, extending in the extending direction. A side surface 512A of the base element 512 is connected to the inflatable portion 3B of the balloon 3. A side surface 511A of the base element 511 is connected to a side surface 512B opposite of the side surface 512A of the base element 512. The side surface 52A of the tip end portion 52 is connected to a side surface 511B opposed to the side surface 511A of the base element 511.

The length of the base element 511 in the orthogonal direction is shorter than the length of the base element 512 in the orthogonal direction. The length of the side surface 52A of the tip end portion 52 is shorter than the length of the base element 511 in the orthogonal direction. In a cross-section of the protrusion 46G, a portion including both orthogonal end portions of the base elements 511 and 512 and the tip end portion 52 is arranged outside of the virtual triangle T1. The length of the base portion 51 in the protruding direction is longer than the length of the tip end portion 52 in the protruding direction.

The protrusion 46G can stably support the tip end portion 52 by the base portion 51. Therefore, the protrusion 46G allows the tip end portion 52 of the protrusion 46G to suitably dig into the stenotic lesion 90A when the balloon 3 inflates.

Figure 13B:
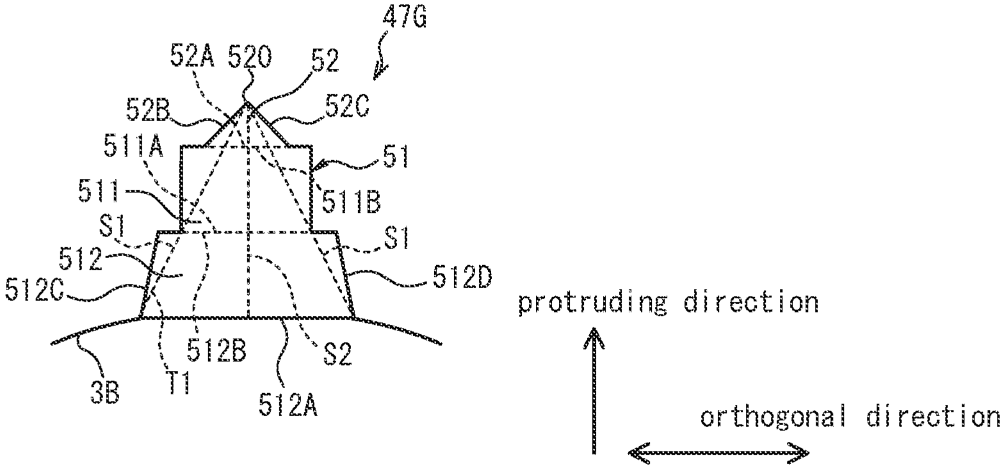
FIG. 13B is a view of a protrusion.

The protrusion 47G shown in FIG. 13B differs from the protrusion 46G (refer to FIG. 13A) in terms of the shape of the base element 512. The shape of the base element 512 is a prism with a trapezoidal cross-section. The side surface 512B of the base element 512 is shorter than the side surface 512A of the base element 512. Note that the side surface 512B is longer than the side surface 511A of the base element 511.

Of the base element 512, side surfaces 512C and 512D, excluding the side surfaces 512A and 512B, are defined. The direction extending from the side surface 512A side to the side surface 512B side along the side surfaces 512C and 512D is inclined toward the virtual center S2 that passes through the apex 520. In a cross-section of the protrusion 47G, portions including both end portions in the orthogonal direction of the tip end portion 52 and the base elements 511 and 512 are arranged outside of the virtual triangle T1.

Figure 13C:
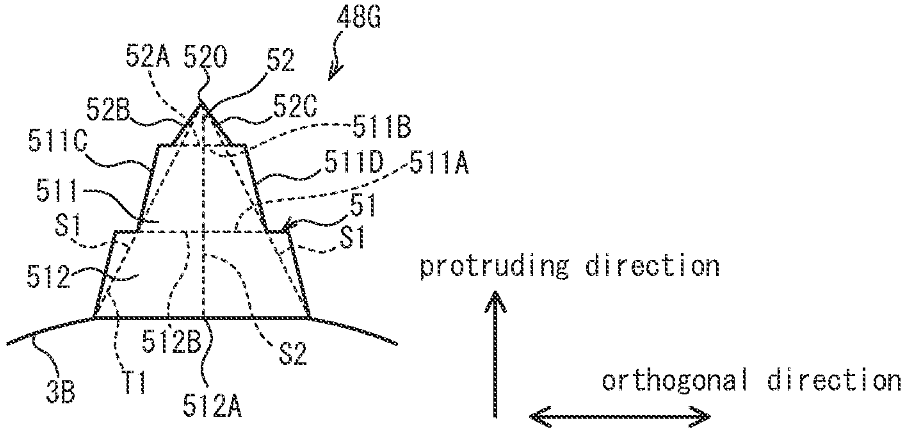
FIG. 13C is a view of a protrusion.

The protrusion 48G shown in FIG. 13C differs from the protrusion 47G (refer to FIG. 13B) in terms of the shape of the base element 511. The shape of the base element 511 is a prism with a trapezoidal cross-section. The side surface 511B of the base element 511 is shorter than the side surface 511A of the base element 511. Note that the side surface 511B is longer than the side surface 52A of the tip end portion 52.

Of the base element 511, side surfaces 511C and 511D, excluding the side surfaces 511A and 511B, are defined. The direction extending from the side surface 511A side to the side surface 511B side along the side surfaces 511C and 511D is inclined toward the virtual center S2 that passes through the apex 520. In a cross-section of the protrusion 48G, portions including both end portions in the orthogonal direction of the tip end portion 52 and the base elements 511 and 512 are arranged outside of the virtual triangle T1.

With the protrusions 47G and 48G, the tip end portion 52 can be more stably supported by the base portion 51. Therefore, the protrusions 47G and 48G can appropriately apply each of the tip end portions 52 to the stenotic lesion 90A when the balloon 3 inflates. Also, with the protrusions 47G and 48G, the step of the side surface in the orthogonal direction can be smaller, so the protrusions 47G and 48G will not easily fall over even if the protrusion amount of the protrusions 47G and 48G is large. Consequently, by making the protrusion amount of the protrusions 47G and 48G large, the protrusions 47G and 48G can appropriately dig into the stenotic lesion 90A when the balloon 3 inflates.

Seventh Embodiment (Balloon Catheter 1G)

Figure 14:
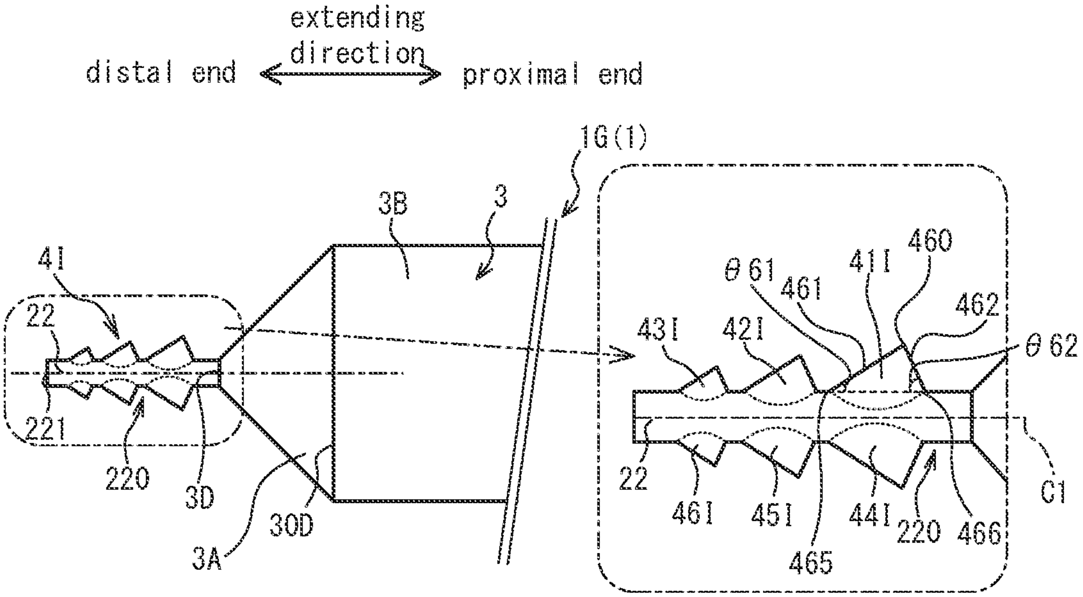
FIG. 14 is an enlarged view of an area near the distal end connecting portion 3A of a balloon catheter.

The balloon catheter 1G will now be described with reference to FIG. 14. The balloon catheter 1G differs from the balloon catheter 1A in that it does not have the protruding portion 4A and has a protruding portion 4I instead of the protruding portion 4B. Hereinafter, a description of the structure of the balloon catheter 1G that is the same as that of the balloon catheter 1A will be omitted.

The protruding portion 4I has protrusions 41I, 42I, 43I, 44I, 45I, and 46I. The protrusions 41I to 46I are provided on the outer surface of the distal end extending portion 220 of the inner tube 22 and protrude outward. The protrusions 41I, 42I, and 43I are arranged along the extending direction. The positions of the 41I, 42I, and 43I in the circumferential direction coincide. The protrusions 44I, 45I, and 46I are arranged along the extending direction. The positions of the protrusions 44I, 45I, and 46I in the circumferential direction coincide. The protrusions 41I, and 44I are near the distal end portion 30D of the balloon 3. The protrusions 43I and 46I are near the distal end portion 221 of the inner tube 22. The protrusions 41I and 44I face each other across the center axis C1. The protrusions 42I and 45I face each other across the center axis C1. The protrusions 41I and 44I face each other across the center axis C1.

Figure 2:
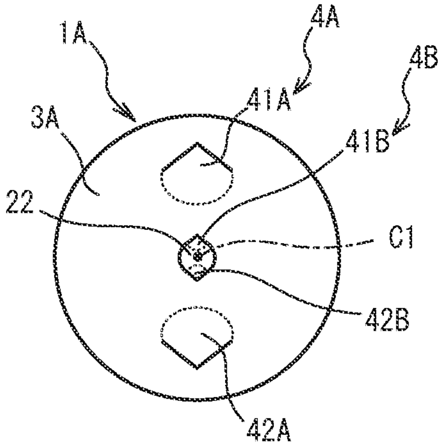
FIG. 2 is a view of the balloon catheter from the distal end side.

There is a similarity relationship between shape of the protrusions 41I to 46I and the shape of the protrusions 41B and 42B of the protruding portion 44B of the balloon catheter 1A (refer to FIG. 1). A distal end portion 465, a proximal end portion 466, a distal end inclined portion 46I, a proximal end inclined portion 462, an apex 460, and angles θ61 and θ62 of each of the protrusions 41I to 46I correspond to the distal end portion 425, the proximal end portion 426, the distal end inclined portion 421, the proximal end inclined portion 422, the apex 420, and the angles θ21 and θ22 of each of the protrusions 41B and 42B of the protruding portion 4B, respectively. The angle θ62 of the proximal end inclined portion 462 with respect to the distal end extending portion 220 is greater than the angle θ61 of the distal end inclined portion 461 with respect to the distal end extending portion 220.

The protrusions 41I, 42I, and 43I differ from each other in terms of the distance, i.e., the protrusion amount, from the distal end extending portion 220 to the apex 460. Of the protrusions 41I, 42I, and 43I, the protrusion amount of the protrusion 43I that is nearest to the distal end portion 221 of the inner tube 22 is the smallest, and the protrusion amount of the protrusion 41I nearest to the distal end portion 3D of the balloon 3 is the largest. The protrusion amount of each of the protrusions 41I, 42I, and 43I becomes larger nearer the distal end portion 3D of the balloon 3.

The protrusions 44I, 45I, and 46I differ from each other in terms of their protrusion amounts. Of the protrusions 44I, 45I, and 46I, the protrusion amount of the protrusion 46I that is nearest to the distal end portion 221 of the inner tube 22 is the smallest, and the protrusion amount of the protrusion 44I nearest to the distal end portion 3D of the balloon 3 is the largest. The protrusion amount of each of the protrusions 44I, 45I, and 46I becomes larger nearer the distal end portion 3D of the balloon 3.

Operations and Effects of Seventh Embodiment

With the balloon catheter 1G, the resistance force that the protruding portion 4I receives from the stenotic lesion 90A when the distal end extending portion 220 of the inner tube 22 advances through the lumen of the stenotic lesion 90A can be suppressed. Therefore, the balloon catheter 1G can reduce the possibility of the balloon 3 being pushed back by the resistance force that the protruding portion 4I receives from the stenotic lesion 90A.

The balloon catheter 1G has the protrusions 41I to 43I and 44I to 46I arranged in the extending direction. Therefore, compared to the balloon catheter 1A having only the protrusions 41A and 41B, the balloon 3 is less likely to be pushed back when the distal end extending portion 220 of the inner tube 22 receives resistance force from the stenotic lesion 90A as it advances through the lumen of the stenotic lesion 90A. Therefore, the balloon catheter 1G can more efficiently perform the operation of gradually advancing the balloon 3 distally while repeatedly changing the balloon 3 between the inflated state and the deflated state.

Special Notes Relating to Seventh Embodiment

The protrusion amounts of the protrusions 41I to 46I may be the same. Also, the protrusion amounts of the protrusions 42I, 43I, 45I, and 46I may be the same, and the protrusion amount of the protrusions 41I and 44I may be less than the protrusion amount of the protrusions 42I, 43I, 45I, and 46I. The positions of the protrusions 41I to 43I in the circumferential direction may be different. Similarly, the positions of the protrusions 44I to 46I in the circumferential direction may be different. The balloon catheter 1G may have the protruding portion 4A on the distal end connecting portion 3A of the balloon 3.

Eighth Embodiment (Balloon Catheter 1H)

Figure 15:
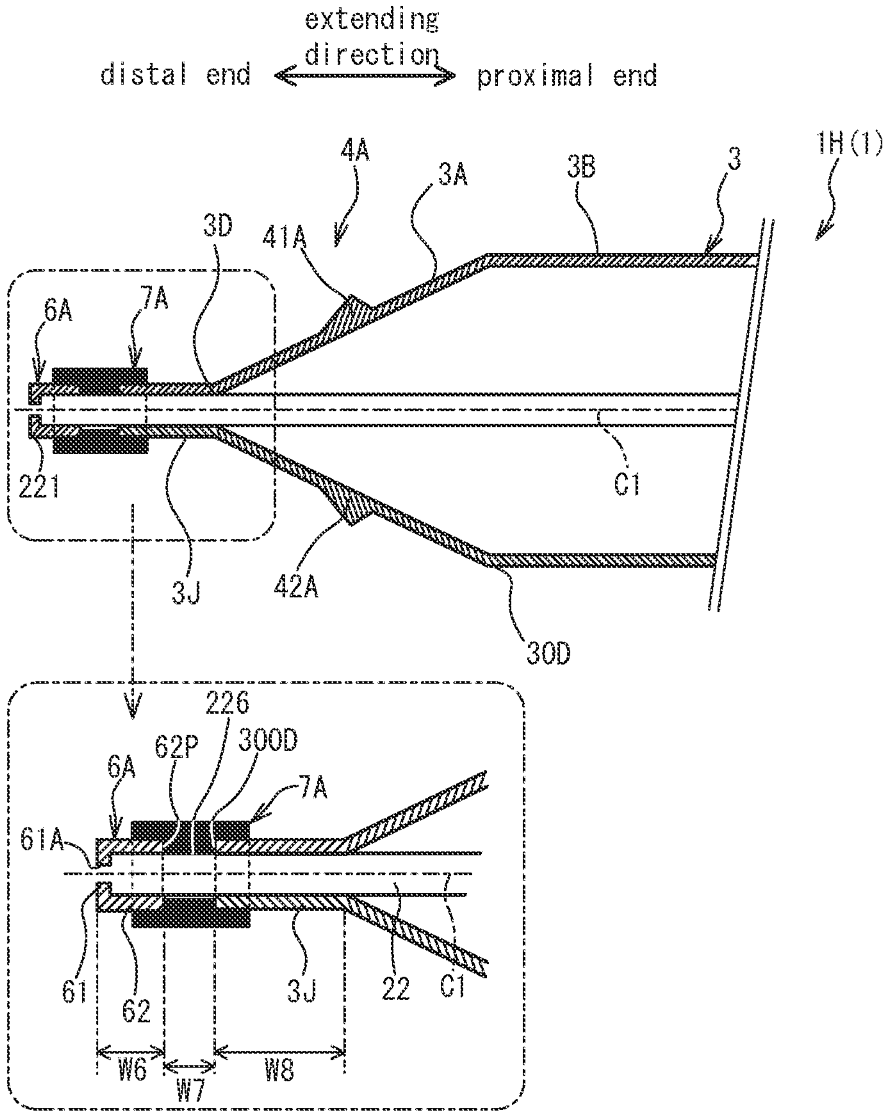
FIG. 15 is an enlarged sectional view of an area of the distal end connecting portion 3A of a balloon catheter.

The balloon catheter 1H will now be described with reference to FIG. 15. The balloon catheter 1H differs from the balloon catheter 1A (refer to FIG. 1) in that the balloon 3 has a distal end joining portion 3J, the balloon catheter 1H has only the protruding portion 4A and does not have the protruding portion 4B, and the balloon catheter 1H further has a distal end tip 6A and a cover tube 7A. Hereinafter, a description of the structure of the balloon catheter 1H that is the same as that of the balloon catheter 1A will be omitted.

The balloon 3 of the balloon catheter 1H has the distal end joining portion 3J extending from the distal end portion 3D of the distal end connecting portion 3A toward the distal end side. The distal end joining portion 3J extends along the outer surface of the inner tube 22 and joins to the inner tube 22. Hereinafter, the end portion on the distal end side of the distal end joining portion 3J will be referred to as a distal end portion 300D.

The distal end tip 6A is provided on the distal end portion 221 of the inner tube 22. The distal end tip 6A is made of flexible resin. The distal end tip 6A prevents the blood vessel 9 from being damaged when the distal end portion 221 of the inner tube 22 strikes the interior wall of the blood vessel 9.

The distal end tip 6A has a cover portion 61 and an extending portion 62. The cover portion 61 covers the distal end portion 221 of the inner tube 22 from the distal end side. A through-hole 61A through which passes a guide wire that is inserted through the inner tube 22 is provided in the cover portion 61. The diameter of the through-hole 61A is smaller than the diameter of the lumen of the inner tube 22. The extending portion 62 extends from the end portion on the outside of the cover portion 61 toward the proximal end side along the outer surface of the inner tube 22. The end portion (hereinafter, referred to as a proximal end portion 62P) on the proximal end side of the extending portion 62 is spaced distally from the distal end portion 300D of the distal end joining portion 3J of the balloon 3. Of the inner tube 22, the portion of the inner tube 22 on the proximal end side of the proximal end portion 62P and on the distal end side of the distal end portion 300D in the extending direction is not covered by the distal end tip 6A or the distal end joining portion 3J. Hereinafter, the portion of the inner tube 22 that is not covered by the distal end tip 6A or the distal end joining portion 3J will be referred to as an exposed portion 226.

The cover tube 7A has a cylindrical shape. The cover tube 7A covers the portion of the extending portion 62 of the distal end tip 6A near the proximal end portion 62P, the portion of the distal end joining portion 3J of the balloon 3 near the distal end portion 300D, and the exposed portion 226 of the inner tube 22 from the outside. The hardness of the cover tube 7A is uniform.

The cover tube 7A, the distal end tip 6A, and the balloon 3 are melted by heat. Heat is applied near the distal end portion of the balloon catheter 1H in the state shown in FIG. 15. Consequently, the cover tube 7A, the portion near the proximal end portion 62P of the extending portion 62 of the distal end tip 6A, and the portion near the distal end portion 300D of the distal end joining portion 3J of the balloon 3 are melted and welded together. Therefore, in FIG. 15, the steps shown at the cover tube 7A, the portion of the extending portion 62 of the distal end tip 6A near the proximal end portion 62P, and the portion of the distal end joining portion 3J of the balloon 3 near the distal end portion 300D are eliminated by the cover tube 7A that has been melted by heating entering the step portion. The same also applies to FIGS. 16A, 16B, and 16C, which will be described later.

Operations and Effects of Eighth Embodiment

When the cover tube 7A is not provided, the hardness of the portion of the balloon catheter 1H on the distal end side of the distal end portion 3D of the balloon 3 differs at each of a region W6 on the distal end side of the proximal end portion 62P in the extending direction, a region W7 between the proximal end portion 62P and the distal end portion 300D, and a region W8 on the proximal end side of the distal end portion 300D. The hardness of the region W7 is softer than the hardnesses of the regions W6 and W8. The reason for this is that the inner tube 22 and the distal end tip 6A are disposed in the region W6, and the inner tube 22 and the distal end joining portion 3J are disposed in the region W8, whereas only the inner tube 22 is disposed in the region W7. Here, the difference in hardness between the regions W6 to W8 is preferably small in order to improve trackability to the guide wire.

In contrast, with the balloon catheter 1H, the cover tube 7A is provided in a position overlapping with the region W7. The hardness of the region W7 is harder than the hardness of the region W6, and the hardness of the region W8 is harder than the hardness of the region W7 (hardness of the region W6<hardness of the region W7<the hardness of region W8). By increasing the hardness of the region W7 with the cover tube 7A, the difference in hardness between the regions W6 and W8, and the region W7 can be reduced. Accordingly, the balloon catheter 1H can improve the trackability to the guide wire in the distal end portion.

Special Notes Relating to Eighth Embodiment

Cover tubes 7B (FIG. 16A), 7C (FIG. 16B), and 7D (FIG. 16C) that are modified examples of the cover tube 7A will now be described.

Figure 16A:
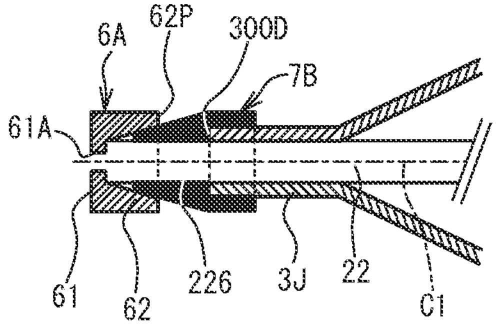
FIG. 16A is a sectional view of a cover tube.

The cover tube 7B shown in FIG. 16A differs from the cover tube 7A that the diameter of a portion of the outer surface increases toward the proximal end side, and that the end portion on the distal end side of the cover tube 7B is positioned to the inside of the extending portion 62 of the distal end tip 6A. Note that the end portion on the distal end side of the cover tube 7B is positioned on the outside of the distal end joining portion 3J of the balloon 3 and covers a portion near the distal end portion 300D of the distal end joining portion 3J, similar to the cover tube 7A.

Figure 16B:
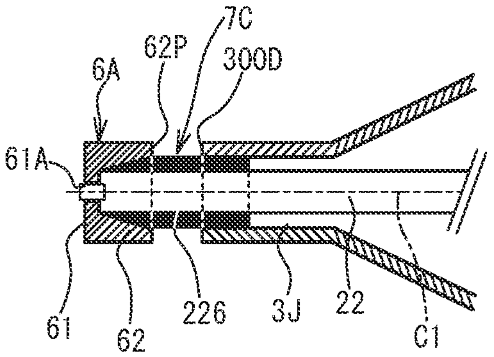
FIG. 16B is a sectional view of a cover tube.

The cover tube 7C shown in FIG. 16B differs from the cover tube 7A in that the end portion on the distal end side of the cover tube 7C is positioned to the inside of the extending portion 62 of the distal end tip 6A, and that the end portion on the proximal end portion of the cover tube 7C is positioned to the inside of the distal end joining portion 3J. In this case, the cover tube 7C extends in the extending direction along the outer surface of the inner tube 22 along the entire region.

Figure 16C:
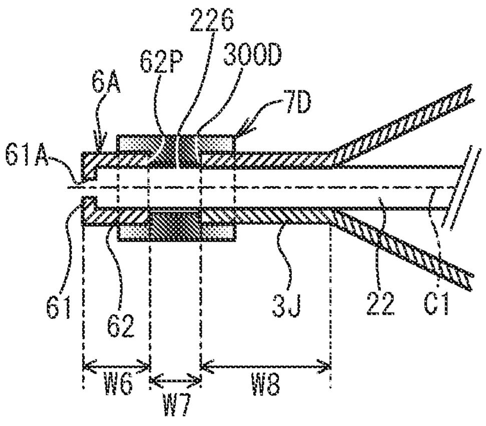
FIG. 16C is a sectional view of a cover tube.

The cover tube 7D shown in FIG. 16C differs from the cover tube 7A in that the hardness is not uniform. The hardness of the cover tube 7D is harder at a portion corresponding to the region W7 than at portions corresponding to the regions W6 and W8. Therefore, the difference in hardness between the regions W6 to W8 of the balloon catheter 1H can be reduced even more, so the trackability to the guide wire at the distal end portion can be improved even more. Note that in the cover tube 7D, the regions W6 to W8 having different hardnesses may be formed by different materials. Also, the hardness may be adjusted by varying the physical properties of the portions of the cover tube 7D, which is made of a common material, corresponding to each of the regions W6 to W8.

Additives for improving slidability may be added to the cover tubes 7A to 7D.

While the invention has been described in conjunction with various example structures outlined above and illustrated in the figures, various alternatives, modifications, variations, improvements, and/or substantial equivalents, whether known or that may be presently unforeseen, may become apparent to those having at least ordinary skill in the art. Accordingly, the example embodiments of the disclosure, as set forth above, are intended to be illustrative of the invention, and not limiting the invention. Various changes may be made without departing from the spirit and scope of the disclosure. Therefore, the disclosure is intended to embrace all known or later developed alternatives, modifications, variations, improvements, and/or substantial equivalents.

What is claimed is:

1. A balloon catheter comprising:

a catheter shaft extending in an extending direction between a first proximal end portion and a first distal end portion;

a balloon connected to the catheter shaft at a position where a distance to the first distal end portion is shorter than a distance to the first proximal end portion, the balloon including an inflatable portion having a cylindrical shape extending in the extending direction, and a distal end connecting portion being a portion extending to a side opposite the inflatable portion from a second distal end portion of the inflatable portion, the second distal end portion being one end portion of the inflatable portion that is closer to the first distal end portion of the catheter shaft than the other end portion of the inflatable portion in the extending direction, a diameter of the end portion of the distal end connecting portion that is connected to the inflatable portion being larger than a diameter of a third distal end portion of the distal end connecting portion which is an end portion on a side opposite the end portion connected to the inflatable portion, the distal end connecting portion connecting to the catheter shaft at the third distal end portion; and a protruding portion protruding radially outward with respect to a center axis of the catheter shaft, the protruding portion having at least one of a first protruding portion including a plurality of protrusions provided on the distal end connecting portion of the balloon, or a second protruding portion including a plurality of protrusions provided on a distal end extending portion which is a portion between the third distal end portion of the balloon and the first distal end portion of the catheter shaft in the extending direction, wherein the distal end connecting portion includes at least a region where a protrusion amount is smaller than a protrusion amount of the protruding portion, between the second distal end portion and an end portion of the protruding portion nearest to the second distal end portion, and wherein the plurality of protrusions of the at least one of the first protruding portion or the second protruding portion are arranged in a circumferential direction around the center axis.

2. The balloon catheter according to claim 1, wherein the protruding portion includes the first protruding portion.

3. The balloon catheter according to claim 2, wherein the first protruding portion includes a first apex protruding farthest outward in a radial direction;

a first distal end inclined portion extending toward the first apex from an end portion on a side near the third distal end portion; and a first proximal end inclined portion extending toward the first apex from an end portion on a side near the second distal end portion, and an angle of the first proximal end inclined portion with respect to the distal end connecting portion is greater than an angle of the first distal end inclined portion with respect to the distal end connecting portion.

4. The balloon catheter according to claim 2, wherein the first protruding portion is provided on a portion including the third distal end portion.

5. The balloon catheter according to claim 2, wherein the protruding portion further includes a third protruding portion provided on the inflatable portion of the balloon, and an inside protruding portion is provided extending between the first protruding portion and the third protruding portion, and protruding inward in a radial direction from an inner surface of the distal end connecting portion.

6. The balloon catheter according to claim 2, wherein the distal end connecting portion has a plurality of inclined portions;

the plurality of inclined portions includes at least two inclined portions having different inclination angles between the center axis and a direction extending from the second distal end portion side toward the third distal end portion side along each inclined portion; and the first protruding portion is provided on the inclined portion having the smallest inclination angle, of the plurality of inclined portions.

7. The balloon catheter according to claim 1, wherein the protruding portion includes the second protruding portion.

8. The balloon catheter according to claim 7, wherein the protrusion amount of each of the plurality of protrusions of the second protruding portion is larger closer to the third distal end portion.

9. The balloon catheter according to claim 7, wherein the second protruding portion includes a second apex protruding farthest outward in a radial direction;

a second distal end inclined portion extending toward the second apex from an end portion on a side near the first distal end portion; and a second proximal end inclined portion extending toward the second apex from an end portion on a side near the third distal end portion, and an angle of the second proximal end inclined portion with respect to the distal end extending portion is greater than an angle of the second distal end inclined portion with respect to the distal end extending portion.

10. The balloon catheter according to claim 1, wherein the distal end extending portion includes at least a region where the protrusion amount is smaller than the protrusion amount of the protruding portion, between the first distal end portion and an end portion nearest to the first distal end portion of the protruding portion.

11. A balloon catheter comprising:

a catheter shaft extending in an extending direction between a first proximal end portion and a first distal end portion;

a balloon connected to the catheter shaft at a position where a distance to the first distal end portion is shorter than a distance to the first proximal end portion, the balloon including an inflatable portion having a cylindrical shape extending in the extending direction, and a distal end connecting portion being a portion extending to a side opposite the inflatable portion from a second distal end portion of the inflatable portion, the second distal end portion being one end portion of the inflatable portion that is closer to the first distal end portion of the catheter shaft than the other end portion of the inflatable portion in the extending direction, a diameter of the end portion of the distal end connecting portion that is connected to the inflatable portion being larger than a diameter of a third distal end portion of the distal end connecting portion which is an end portion on a side opposite the end portion connected to the inflatable portion, the distal end connecting portion connecting to the catheter shaft at the third distal end portion; and a protruding portion protruding radially outward with respect to a center axis of the catheter shaft, the protruding portion having at least one of a first protruding portion provided on the distal end connecting portion of the balloon, or a second protruding portion provided on a distal end extending portion which is a portion between the third distal end portion of the balloon and the first distal end portion of the catheter shaft in the extending direction, wherein the distal end connecting portion includes at least a region where a protrusion amount is smaller than a protrusion amount of the protruding portion, between the second distal end portion and an end portion of the protruding portion nearest to the second distal end portion, wherein the protruding portion includes the first protruding portion, and wherein the first protruding portion has a spiral shape extending in a circumferential direction around the center axis.

* * * * *